US006630609B2

(12) United States Patent  (10) Patent No.: US 6,630,609 B2
Holton et al.  (45) Date of Patent: Oct. 7, 2003

(54) TAXANE SYNTHESIS METHOD AND INTERMEDIATES

(75) Inventors: Robert A. Holton, Tallahassee, FL (US); Phong Vu, Little Falls, NJ (US); Tawfik Gharbaoui, San Diego, CA (US); Vincent Reboul, Caen (FR)

(73) Assignee: Florida State University, Tallahassee, FL (US)

( * ) Notice: Subject to any disclaimer, the term of this patent is extended or adjusted under 35 U.S.C. 154(b) by 0 days.

(21) Appl. No.: 10/196,025

(22) Filed: Jul. 16, 2002

(65) Prior Publication Data

US 2003/0097024 A1 May 22, 2003

Related U.S. Application Data

(60) Continuation of application No. 09/617,555, filed on Jul. 17, 2000, now Pat. No. 6,441,253, which is a division of application No. 09/136,827, filed on Aug. 20, 1998, now Pat. No. 6,111,144.
(60) Provisional application No. 60/056,210, filed on Aug. 21, 1997.

(51) Int. Cl.⁷ .................. C07C 35/20; C07C 49/105; C07C 45/00; C07D 303/00

(52) U.S. Cl. .................. 568/821; 568/822; 568/838; 568/375; 568/374; 568/361; 568/338; 549/512; 549/513

(58) Field of Search ................. 568/338, 361, 568/374, 375, 821, 822, 838; 549/512, 513

(56) References Cited

U.S. PATENT DOCUMENTS

| 4,857,653 A | 8/1989 | Colin et al. |
| 4,924,011 A | 5/1990 | Denis et al. |
| 4,924,012 A | 5/1990 | Colin et al. |
| 4,960,790 A | 10/1990 | Stella et al. |
| 5,015,744 A | 5/1991 | Holton |
| 5,136,060 A | 8/1992 | Holton |
| 5,175,315 A | 12/1992 | Holton |
| 5,200,534 A | 4/1993 | Rao |
| RE34,277 E | 6/1993 | Denis et al. |
| 5,254,703 A | 10/1993 | Holton |
| 5,300,638 A | 4/1994 | Farina et al. |
| 5,336,785 A | 8/1994 | Holton |
| 5,338,872 A | 8/1994 | Holton et al. |
| 5,367,086 A | 11/1994 | Rao |
| 5,393,895 A | 2/1995 | Gaullier et al. |
| 5,393,896 A | 2/1995 | Margraff |
| 5,399,726 A | 3/1995 | Holton et al. |
| 5,405,972 A | 4/1995 | Holton et al. |
| 5,416,225 A | 5/1995 | Danishefsky et al. |
| 5,430,160 A | 7/1995 | Holton |
| 5,449,790 A | 9/1995 | Zheng et al. |
| 5,461,169 A | 10/1995 | Nicolaou et al. |
| 5,466,834 A | 11/1995 | Holton |
| 5,481,007 A | 1/1996 | Nicolaou et al. |
| 5,488,116 A | 1/1996 | Danishefsky et al. |
| 5,508,447 A | 4/1996 | Magnus |
| 5,527,924 A | 6/1996 | Danishefsky et al. |
| 5,576,450 A | 11/1996 | Bouchard et al. |
| 5,578,739 A | 11/1996 | Hittinger |
| 5,587,493 A | 12/1996 | Bouchard et al. |
| 5,589,502 A | 12/1996 | Tsujihara et al. |
| 5,589,592 A | 12/1996 | Horikawa et al. |
| 5,594,157 A | 1/1997 | Gunawardana et al. |
| 5,597,931 A | 1/1997 | Danishefsky et al. |
| 5,599,820 A | 2/1997 | Ojima et al. |
| 5,606,083 A | 2/1997 | Bouchard et al. |
| 5,608,073 A | 3/1997 | Tsujihara et al. |
| 5,608,102 A | 3/1997 | Bourzat et al. |
| 5,616,739 A | 4/1997 | Mas et al. |
| 5,616,740 A | 4/1997 | Klein et al. |
| 5,618,952 A | 4/1997 | Holton et al. |
| 5,621,121 A | 4/1997 | Commercon et al. |
| 5,654,447 A | 8/1997 | Holton et al. |
| 5,670,658 A | 9/1997 | Bastart et al. |

(List continued on next page.)

FOREIGN PATENT DOCUMENTS

WO  WO 95/03265 A1  2/1995
WO  wO 97/42181 A1  11/1997

OTHER PUBLICATIONS

Chaudhary et al. "Synthesis of 10–Deacetoxytaxol and 10–Deoxytaxotere" Tetrahedron Letters, vol. 34, No. 31 (1993) pp. 4921–4924.

(List continued on next page.)

Primary Examiner—Johann Richter
Assistant Examiner—Sikarl A. Witherspoon
(74) Attorney, Agent, or Firm—Senniger, Powers, Leavitt & Roedel

(57) ABSTRACT

A process for the preparation of a composition having the formula:

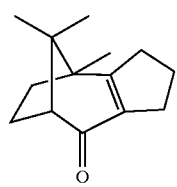

5 in which a compound having the formula:

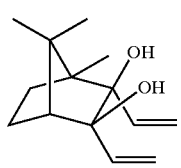

4 is treated with a base and a silylating agent.

5 Claims, No Drawings

U.S. PATENT DOCUMENTS

| | | | |
|---|---|---|---|
| 5,675,025 | A | 10/1997 | Sisti et al. |
| 5,677,462 | A | 10/1997 | Mas et al. |
| 5,677,470 | A | 10/1997 | Tsujihara et al. |
| 5,688,977 | A | 11/1997 | Sisti et al. |
| 5,703,247 | A | 12/1997 | Kingston et al. |
| 5,760,252 | A | 6/1998 | Holton et al. |

OTHER PUBLICATIONS

Chen et al. "Taxol Structure–Activity Relationships: Synthesis and Biological Evaluation of 2–Deoxytaxol" Tetrahedron Letters vol. 34, No. 20 (1993) pp. 3205–3206.

Chen et al. "Synthesis of 7–deoxy– and 7, 10–Dideoxytaxol via Radical Intermediates" J. Org. Chem. vol. 58, No. 19 (1993) pp. 5028–5029.

Chen et al. "Taxol Structure–Activity Relationships: Synthesis and Biological Evaluation of 10–Deoxytaxol" J. Org. Chem., vol. 58, No. 11 (May 21, 1993) pp. 2927–2928.

Denis et al. "A Highly Efficient, Practical Approach to Natural Taxol", J. Am Chem. Soc. vol. 110, No. 17, (1988) pp. 5917–5919.

Georg et al., Taxane Anticancer Agents, Basic Science and Current Status, Chapter 2 Paclitaxel: From Discovery to Clinic, Chapter 21 The Total Synthesis of Paclitaxel Starting with Camphor, Chapter 22 The Total Synthesis of Paclitaxel by Assembly of the Ring System, ACS Symposium Series 583, USA (1995), pp. 18–30, 288–301, 302–312.

Holton et al., Synthesis of the Taxane Ring System, J. Am. Chem. Soc., vol. 106 (1984) pp. 5731–5732.

Holton et al., A Synthesis of Taxusin, J. Am. Chem. Soc., vol. 110 (1988) pp. 6558–6560.

Holton et al., First Total Synthesis of Taxol. 1. Functionalization of the B Ring, J. Am. Chem. Soc., vol. 116, No. 4 (1994) pp. 1597–1598.

Holton et al., First Total Synthesis of Taxol. 2. Completion of the C and D Rings, J. Am. Chem. Soc., vol. 116, No. 4 (1994) pp. 1599–1600.

Holton et al. "A Simple Synthesis of 10–deacetoxytaxol Derivatives" (Nov. 22, 1993) pp. 2–5.

Kingston et al., "The Chemistry of Taxol, a Clinically Useful Anticancer Agent" Journal of Natural Products, vol. 53, No. 1 (1990) pp. 1–12.

Klein "Synthesis of 9–Dihydrotaxol: A Novel Bioactive Taxane", Tetrahedron Letters, vol. 34, No. 13 (1993) pp 2047–2050.

Leriverend et al. Bull. Soc. Chim. Fr. (1970) p. 1060.

Magri et al. "Modified Taxols, 4. Synthesis and Biological Activity of Taxols Modified in the Side Chain" Journal of Natural Products, vol. 51, No. 2 (1988) pp. 298–306.

Mangatal et al. "Application of the Vicinal Oxyamination Reaction with Asymmetric Induction to the Hemisynthesis of Taxol and Analogs" Tetrahedron Letters, vol. 45, No. 13 (1989) pp. 4177–4190.

Nicolaou et al., A Convergent Strategy Towards Taxol. A Facile Enantioselective Entry Into a Fully Functionalized Ring A System, J. Chem. Soc., Chem. Commun., (1992), pp. 1117–1118.

Nicolaou et al., Synthesis of a Fully Functionalized CD Ring System of Taxol, J. Chem. Soc., Chem. Commun., (1992), pp. 1118–1120.

Ojima et al. "New and Efficient Approaches to the Semisynthesis of Taxol and its C–13 Side–Chain Analogs by Means of β–Lactam Synthon Method" Tetrahedron, vol. 48, No. 34 (1992) pp. 6985–7012.

Ojima et al. "Synthesis and Biological Activity of 3'–alkyl– and 3'–alkenyl–3'–dephenyldocetaxels" Bioorganic and Medicinal Chemistry Letters, vol. 4, No. 21 (1994) pp. 2631–2634.

Ojima et al. "Synthesis and Structure–Activity Relationships of New Antitumor Taxoids. Effects of Cycloexyl Substitution at the C–3' and/or C–2 of Texotere(Docetaxel)" J. Med. Chem., vol. 37 (1994) pp. 2602–2608.

Senilh et al. "Chime Organique Biologique–Hemisynthesis de nouveaux analogues du taxol. Etude de leur interaction avec la tubuline" C.R. Acad. Sci. Paris, Serie II, t. 299, No. 15 (1984) pp. 1039–1043.

TAXANE SYNTHESIS METHOD AND INTERMEDIATES

REFERENCE TO RELATED APPLICATIONS

This application is a continuation application based on U.S. Ser. No. 09/617,555, filed Jul. 17, 2000, now U.S. Pat. No. 6,441,253, which is a divisional application based on U.S. Ser. No. 09/136,827, filed Aug. 20, 1998, now U.S. Pat. No. 6,111,144, which claims benefit of U.S. Provisional Application Serial No. 60/056,210, filed Aug. 21, 1997, now expired.

This invention was made with government support under NIH Grant #CA 42031 awarded by the National Institutes of Health. The Government has certain rights in the invention.

SUMMARY OF THE INVENTION

The present invention is directed to a process for the preparation of baccatin III, taxol, docetaxel and their analogs from borneol (1) and camphor (2), commonly known articles of commerce.

Processes for the total synthesis of taxol and other tetracyclic taxanes from commodity chemicals have been proposed. For example, in U.S. Pat. No. 5,405,972, Holton et al. disclose a process for the synthesis of taxol and other tetracyclic taxanes from β-patchouline epoxide which, in turn, may be obtained from borneol (1) and camphor (2). Yields obtained by these processes, however, leave some room for improvement.

Leriverend and Conia (*Bull. Soc. Chim. Fr.*, 1970, 1060) observed that diol 4 (which is readily prepared from either camphor or borneol) when heated to 220° C. for a period of one hour rearranged to provide a mixture of ketones 5 and 6 in a ratio of 1:2. Ketone 5 is of great utility in the synthesis of taxanes.

The preparation of diol 4 and ketones 5 and 6 is illustrated in Reaction Scheme 1.

Briefly, therefore, the present invention is directed to a process for the preparation of ketone 5 in relatively high yield and without contamination with ketone 6. The process comprises treating a compound having the formula:

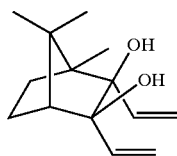

4 with a base and a silylating agent to form a compound having the formula:

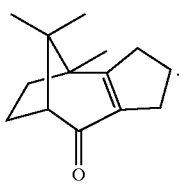

5

The present invention is further directed to a process for converting ketone 5 into taxol, docetaxel, and other taxanes. According to this process, a derivative of ketone 5 having the formula:

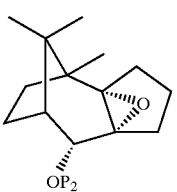

12 is treated with an alkyl metal species, preferably tert-butyllithium, or is treated with a Lewis acid, preferably

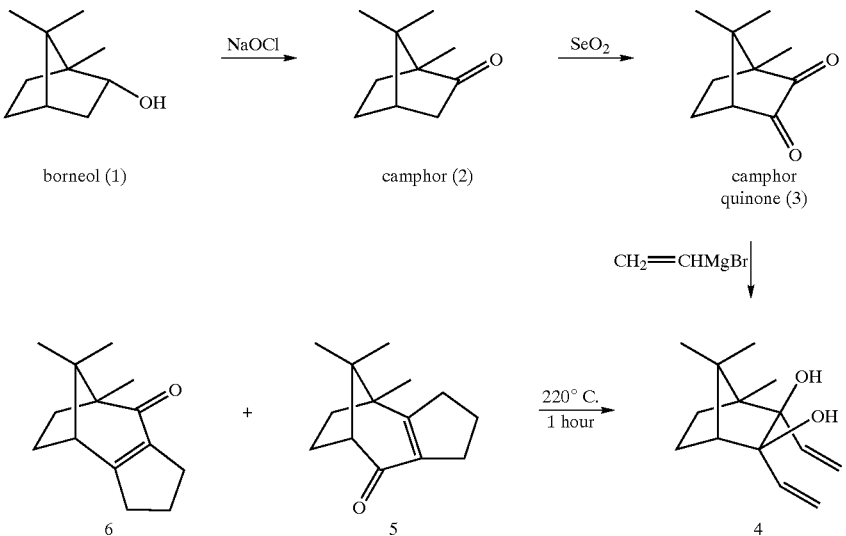

Reaction Scheme 1

TMSOTf, in the presence of a tertiary amine base, preferably triethylamine, to form a compound having the formula:

13

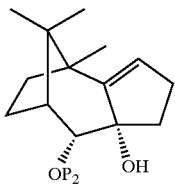

wherein P$_2$ is hydrogen or a hydroxyl protecting group. The process for converting ketone 5 into taxol, docetaxel, and other taxanes may additionally comprise treating a compound having the formula:

14

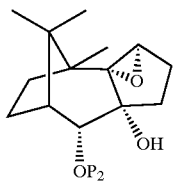

with a Lewis acid, preferably TMSOTf, in the presence of a tertiary amine base, preferably triethyl amine, to form a compound having the formula:

15

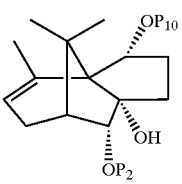

wherein P$_2$ and P$_{10}$ are independently hydrogen or a hydroxyl protecting group.

The present invention is additionally directed to the following intermediates having the formulae

7

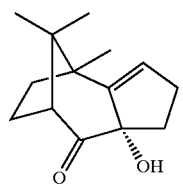

8

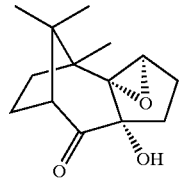

-continued

9

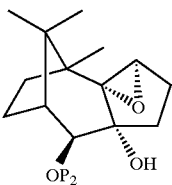

10

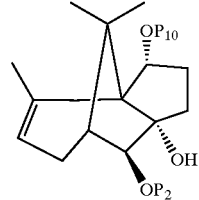

11

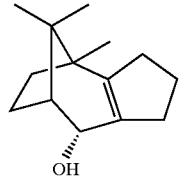

12

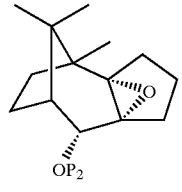

13

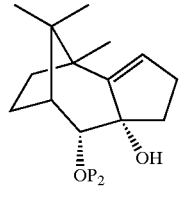

14

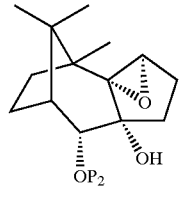

15

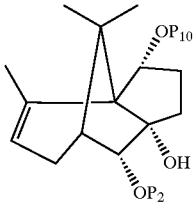

16

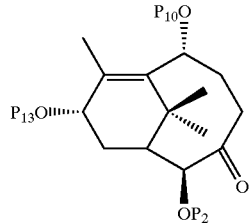

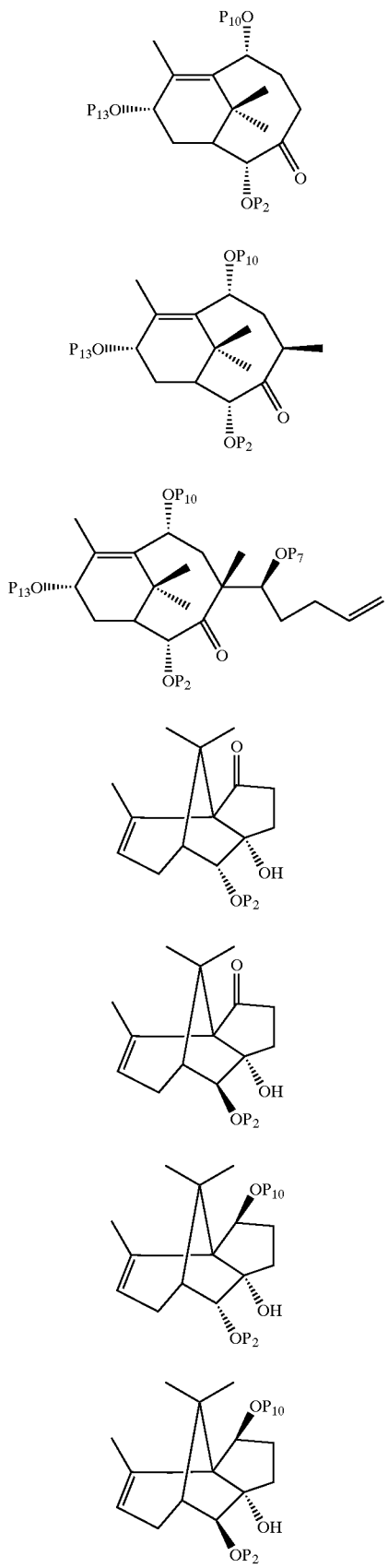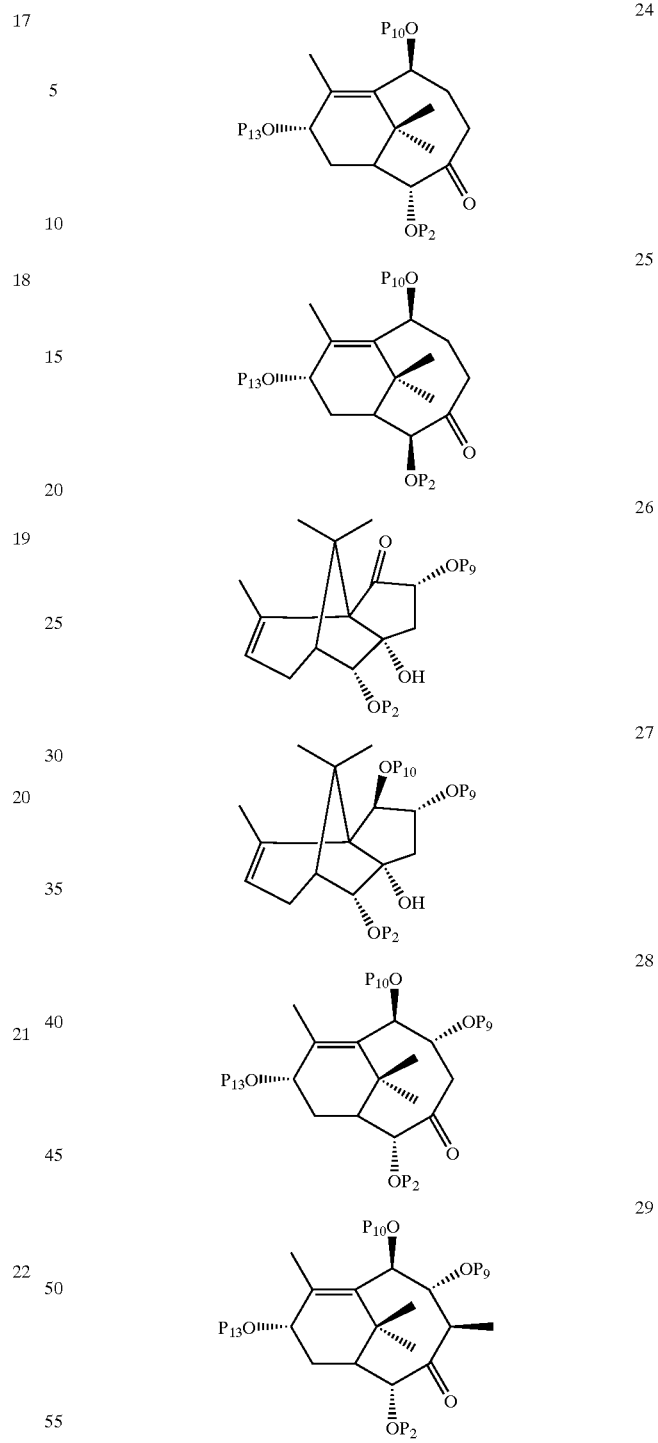

wherein $P_2$, $P_9$, $P_{10}$ and $P_{13}$ are independently selected from hydrogen and hydroxy protecting groups. Compounds containing one or more hydroxy protecting groups can be converted to their hydroxy group analogs by removing such hydroxy protecting groups using standard methods. The compounds identified above are key intermediates in the synthesis of baccatin III, 1-deoxy baccatin III, taxol, 1-deoxy taxol, docetaxel, 1-deoxy docetaxel, and the analogs of these compounds.

Other objects and features of this invention will be in part apparent and in part pointed out hereinafter.

DETAILED DESCRIPTION OF THE PREFERRED EMBODIMENTS

The present invention provides a process for the preparation of ketone 5 in high yield relative to its isomer 6. When diol 4 is treated with a base in the presence of a silylating agent, ketone 5 can be obtained in greater than 95% yield. The base employed is preferably stronger than an alkoxide base. More preferably, the base is a hydride base or an amide base. Still more preferably, the base is potassium hydride or potassium hexamethyldisilazide. The base is preferably non-reactive with the silylating agent selected for the reaction.

Silylating agents for the reaction include those compounds comprising the group —$SiR_1R_2R_3$ wherein $R_1$, $R_2$ and $R_3$ are independently substituted or unsubstituted $C_{1-6}$ alkyl, $C_{2-6}$ alkenyl, $C_{2-6}$ alkynyl, monocyclic aryl or monocyclic heteroaryl. Such silylating agents may further comprise a hydride or triflate group, for example tri(hydrocarbyl)silyl halides and tri(hydrocarbyl)silyl triflates. The hydrocarbon moieties of these silylating agents may be substituted or unsubstituted and preferably are substituted or unsubstituted alkyl or aryl. Trialkylsilyl halides are more preferred with alkyl groups containing from one to four carbon atoms. Still more preferably, the silylating agent is triethylsilyl chloride. Ethereal solvents are preferred for the reaction, with THF being the more preferred solvent.

While the temperature at which the reaction is carried out is not narrowly critical, the temperature may affect the overall yield of the reaction. Preferably, the temperature of the reaction is maintained below about 50° C.; more preferably, the temperature is maintained at or below about 25° C.; even more preferably, the temperature initially is maintained at or below about 0° C. and subsequently is maintained at or below about 25° C. As illustrated in the Examples, these latter conditions produced ketone 5 in 96% yield.

Likewise, the sequence of addition of diol 4, the base and the silylating agent is flexible. For example, diol 4, the base and the silylating agent may be combined at the beginning of the process and reacted in essentially a single step, or these reagents may be combined as described in the Examples.

The reagents for the foregoing reaction (as well as the reagents for the reactions subsequently discussed in this application) are preferably provided in approximately stoichiometric amounts, although various ratios of the reagents can be effectively employed.

Without being bound to any specific theory, it is believed based upon the evidence to date that the base operates to deprotonate the two hydroxy groups of diol 4. The less-sterically-hindered deprotonated hydroxy group (which corresponds to the front hydroxy group of the structure of diol 4 illustrated in Reaction Scheme 1) then reacts with the silylating agent to form a protected hydroxy group. The other deprotonated hydroxy group (which corresponds to the rear hydroxy group of the structure of diol 4 illustrated in Reaction Scheme 1) does not react with the silylating agent. The protected diol 4 then undergoes the oxy-Cope rearrangement to provide a nine-membered ring containing a silyl enol ether and an enolate. Upon the addition of water the enolate is protonated and the subsequent aldol condensation is directed by the position of the silyl enol ether to provide ketone 5.

Ketone 5 can be further converted to other useful taxane synthetic intermediates as shown below.

As shown in reaction scheme 2, treatment of ketone 5 with an amide base, preferably an alkali metal amide base and more preferably LHMDS, in an ethereal solvent, preferably THF, and then with a hydroxylating agent, preferably an oxaziridine and more preferably phenylsulfonyl oxaziridine, provides allylic alcohol 7. Allylic alcohol 7 in the presence of an epoxidizing agent, preferably a peroxy acid and more preferably m-chloroperbenzoic acid, is converted to epoxide 8. Epoxide 8 can be reduced stereoselectively to diol 9 ($P_2$=H), using a hydride reducing agent, preferably a borohydride and more preferably sodium borohydride. The secondary hydroxyl group of 9 can be protected with any of a variety of protecting groups, using standard methods for their attachment. Treatment of 9 with a Lewis acid in the presence of a tertiary amine base, preferably triethyl amine, causes its rearrangement to give 10. In general, the Lewis acids that can be used include triflates and halides of elements of groups IB, IIB, IIIB, IVB, VB, VIB, VIIB, VIII, IIIA, IVA, lanthanides, and actinides (American Chemical Society format), with a preferred Lewis acid being TMSOTf. The second secondary hydroxyl group of 10 can be protected with any of a variety of protecting groups so that $P_{10}$ and $P_2$ may be the same or different and readily chemically distinguishable from each other.

Reaction Scheme 2

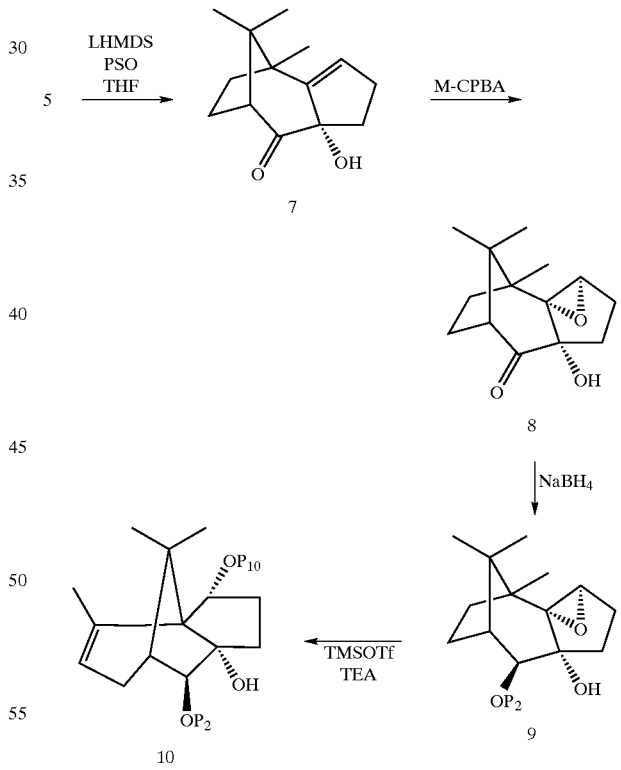

Alternatively, as shown in reaction scheme 3, treatment of ketone 5 with a hydride reducing agent, preferably a borohydride and more preferably sodium borohydride, in the presence of a Lewis acid, preferably a lanthanide metal halide or triflate and more preferably a samarium or cerium halide, selectively furnishes allylic alcohol 11, which undergoes epoxidation from the α-face in the presence of peracids such as m-chloroperbenzoic acid (or hydroperoxides such as tert-butyl hydroperoxide in the presence of metal catalysts or promoters such as titanium (+4) or vanadium (+5) to give epoxide 12 ($P_2$=H). The secondary hydroxyl group of 12 can be protected with any of a variety of protecting groups, using standard methods for their attachment. The epoxide ring of 12 can be opened to provide allylic alcohol 13, using either an alkyl metal species, preferably an alkyllithium and more preferably tert-butyllithium, or a Lewis acid, in the presence of a tertiary amine base, preferably triethylamine. In general the Lewis acids that can be used include triflates and halides of elements of groups IB, IIB, IIIB, IVB, VB, VIB, VIIB, VIII, IIIA, IVA, lanthanides, and actinides (American Chemical Society format), with a preferred Lewis acid being TMSOTf. Allylic alcohol 13 again undergoes epoxidation from the α-face in the presence of peracids such a m-chloroperbenzoic acid (or hydroperoxides such as tert-butyl hydroperoxide in the presence of metal catalysts or promoters such as titanium (+4) and vanadium (+5)) to give epoxide 14. Treatment of 14 with a Lewis acid in the presence of a tertiary amine base, preferably triethyl amine, causes its rearrangement to give 15. In general the Lewis acids that can be used include triflates and halides of elements of groups IB, IIB, IIIB, IVB, VB, VIB, VIIB, VIII, IIIA, IVA, lanthanides, and actinides (American Chemical Society format), with a preferred Lewis acid being TMSOTf. The second secondary hydroxyl group of 15 can be protected with any of a variety of protecting groups so that $P_{10}$ and $P_2$ may be the same or different and readily chemically distinguishable from each other.

It should be noted that 15 is the C(2) epimer of 10.

Alcohols 10 and 15 undergo the "epoxy alcohol fragmentation" to provide 16 and 17, respectively ($P_{13}$=H), which possess the taxane AB ring structure. The epoxy alcohol fragmentation is carried out by first treating the substrate with an epoxidizing agent, then warming the product in the presence of a metal salt. The epoxidizing agent preferably is a peroxy acid such as m-chloroperbenzoic acid (or a hydroperoxide such as tert-butyl hydroperoxide in the presence of metal catalysts or promoters such as titanium (+4) or vanadium (+5)). The preferred metal salt is a halide or alkoxide of a group IA, IIA, IIIB, IVB, VB, VIB, VIIB or VIII metal, with a preferred metal salt being titanium tetraisopropoxide. More preferably, the epoxidizing agent is tert-butyl hydroperoxide in the presence of titanium tetraisoprepoxide. The C(13) secondary hydroxyl group of 16 and 17 can be protected with any of a variety of protecting groups so that $P_{13}$, $P_{10}$ and $P_2$ may be the same or different and readily chemically distinguishable from each other.

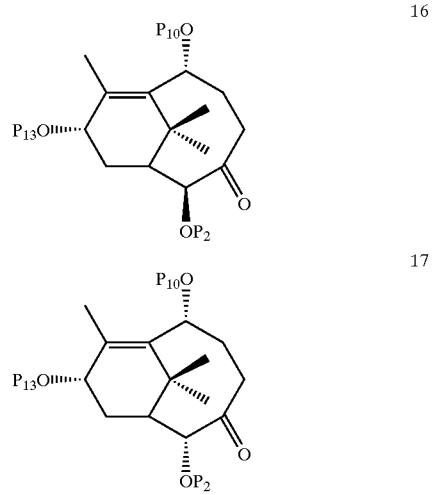

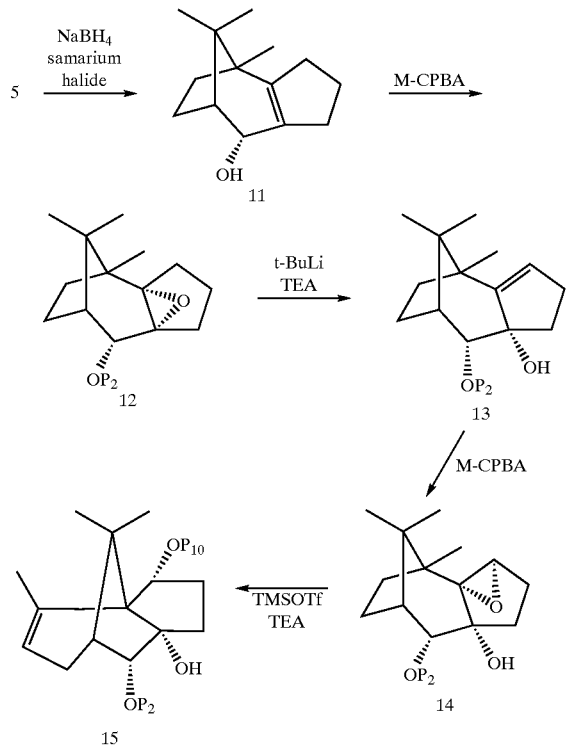

Reaction Scheme 3

Treatment of 17 ($P_2$, $P_{10}$, and $P_{13}$=hydroxyl protecting groups) with a potassium base and methyl iodide provides 18, having the β configuration of the newly introduced methyl group, as shown in reaction scheme 4. The preferred potassium base is potassium hexamethyldisilazide, the preferred solvent is tetrahydrofuran, and the preferred temperature is –5° C. to 0° C. Treatment of 18 ($P_2$, $P_{10}$, and $P_{13}$=hydroxyl protecting groups) with a base followed by 4-pentenal provides 19 ($P_2$, $P_{10}$, $P_{13}$=hydroxyl protecting groups and $P_7$=H). Preferred bases are chosen from lithium and magnesium amides with bromomagnesium diisopropyl amide (BMDA) being a more preferred base. The preferred solvent is tetrahydrofuran and the preferred temperature is between –45° C. and 0° C. The C7 hydroxyl group of 19 can be protected with a variety of hydroxyl protecting groups. For example, treatment of 19 with phosgene and pyridine then ethanol, followed by selective removal of $P_2$, provides an intermediate (19, $P_2$=H, $P_7$=$CO_2Et$, $P_{10}$=TES, and $P_{13}$=TBS) used in the total synthesis of baccatin III and taxol (See, e.g., *J. Amer. Chem. Soc.*, 1994, 116, 1597–1600).

Reaction Scheme 4

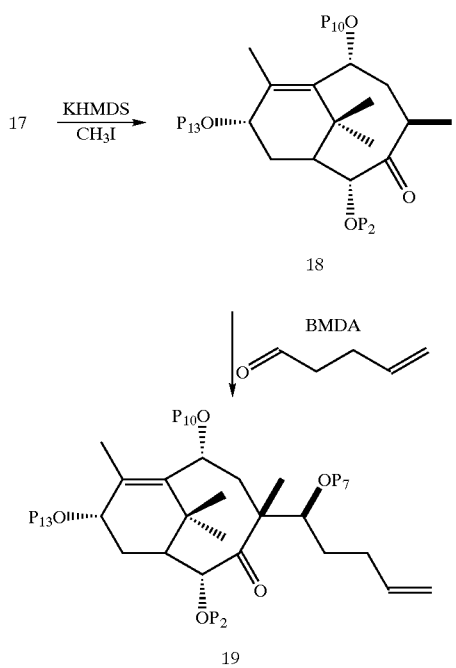

Also, oxidation of 10 ($P_{10}$=H) and 15 ($P_{10}$=H) with any of a variety of standard oxidizing agents provides, respectively, 21 and 20, shown in reaction scheme 5. Preferred oxidizing agents are chromium based reagents. Pyridinium dichromate is a particularly preferred oxidizing agent. Reduction of 21 and 20 with hydride reducing agents provides 23 ($P_{10}$=H) and 22 ($P_{10}$=H), respectively. Preferred reducing agents are chosen from the group of borohydrides and aluminohydrides with lithium aluminum hydride being a more preferred reducing agent. The newly introduced secondary hydroxyl group of 23 ($P_{10}$=H) and 22 ($P_{10}$=H) can be protected with any of a variety of protecting groups so that $P_{10}$ and $P_2$ may be the same or different and readily chemically distinguishable from each other. Alcohols 23 and 22 undergo the "epoxy alcohol fragmentation" to provide 25 and 24 respectively ($P_{13}$=H), which possesses the taxane AB ring structure. The C(13) secondary hydroxyl group of 24 and 25 can be protected with any of a variety of protecting groups so that $P_{13}$, $P_{10}$ and $P_2$ may be the same or different and readily chemically distinguishable from each other.

Reaction Scheme 5

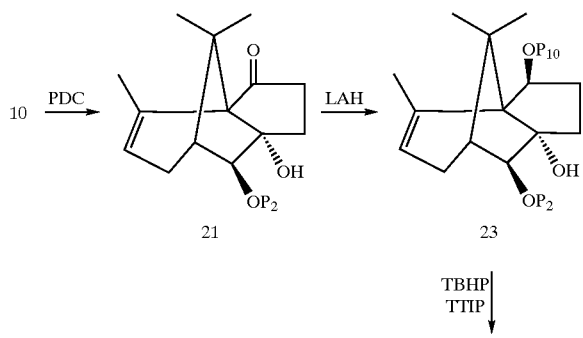

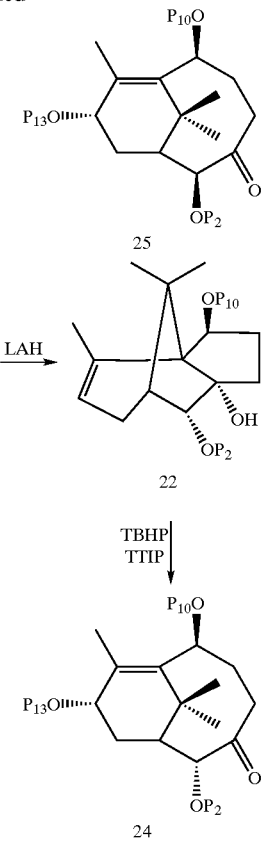

Ketone 20 may be further oxidized to provide a more advanced taxane synthetic intermediate, as shown in reaction scheme 6. Treatment of 20 with an amide base and a tri(hydrocarbon)silyl halide or triflate provides an intermediate silyl enol ether, which is treated directly with a peracid to give 26 ($P_9$=H). The preferred amide base is an alkali metal amide base and more preferably is LDA. The preferred tri(hydrocarbon)silyl halide or triflate is a trialkylsilyl chloride with triethyl silyl chloride being particularly preferred. The preferred peracid may include peroxy carboxylic acids with m-chloroperbenzoic acid being particularly preferred. The C(9) secondary hydroxyl group of 26 can be protected with any of a variety of protecting groups so that $P_9$, $P_{10}$ and $P_2$ may be the same or different and readily chemically distinguishable from each other. Reduction of 26 with hydride reducing agents provides 27 ($P_{10}$=H). Preferred reducing agents are chosen from the group of borohydrides and aluminohydrides; the most preferred reducing agent is lithium aluminum hydride. The newly introduced secondary hydroxyl group of 27 ($P_{10}$=H) can be protected with any of a variety of protecting groups so that $P_{10}$, $P_9$ and $P_2$ may be the same or different and readily chemically distinguishable from each other. Alcohol 27 undergoes the "epoxy alcohol fragmentation" to provide 28 ($P_{13}$=H), having the taxane AB ring structure. The C(13) secondary hydroxyl group of 2 can be protected with any of a variety of protecting groups so that $P_{13}$, $P_{10}$, $P_9$ and $P_2$ are the same or different and readily chemically distinguishable from each other. Treatment of 28 with an amide base, preferably an alkali metal amide base and more preferably LHMDS, and a methyl halide or sulfonate, preferably methyl iodide, in an ethereal solvent, preferably THF, provides 29, which has been used as an intermediate in the total synthesis of C(1) deoxy baccatin III (See, e.g., PCT patent application Ser. No. PCT/US97/07569, International Publication No. WO 97/42181).

Reaction Scheme 6

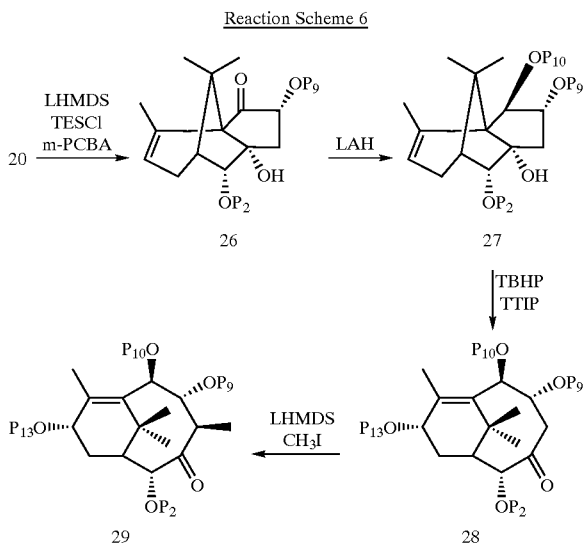

Definitions

As used herein, the term "LHMDS" means lithium hexamethyldisilazide; "KHMDS" means potassium hexamethyldisilazide; "LDA" means lithium diisopropyl amide; "BMDA" means bromomagnesium diisopropyl amide; "PSO" means phenylsulfonyl oxaziridine; "THF" means tetrahydrofuran; "mCPBA" means meta-chloroperbenzoic acid; "TES" means triethylsilyl; "TMS" means trimethylsilyl; "Tf" means —$SO_2CF_3$; "TEA" means triethylamine; "t-BuLi" means tert-butyllithium; "PDC" means pyridinium dichromate; "LAH" means lithium aluminum hydride; "TBHP" means tert-butyl hydroperoxide; "TTIP" means titanium tetraisoprepoxide; "protected hydroxy" means —OP wherein P is a hydroxy protecting group; and "hydroxy protecting group" includes, but is not limited to, acetals having two to ten carbons, ketals having two to ten carbons, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-tri-chloroethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl, protecting groups may be found in "Protective Groups in Organic Synthesis" by T. W. Greene, John Wiley and Sons, 1981, and Second Edition, 1991.

The "hydrocarbon" moities described herein are organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Preferably, these moieties comprise 1 to 20 carbon atoms.

The alkyl groups described herein are preferably lower alkyl containing from one to six carbon atoms in the principal chain and up to 20 carbon atoms. They may be straight or branched chain and include methyl, ethyl, propyl, isopropyl, butyl, hexyl and the like. They may be substituted with aliphatic or cyclic hydrocarbon radicals or hetero-substituted with the various substituents defined herein.

The alkenyl groups described herein are preferably lower alkenyl containing from two to six carbon atoms in the principal chain and up to 20 carbon atoms. They may be straight or branched chain and include ethenyl, propenyl, isopropenyl, butenyl, isobutenyl, hexenyl, and the like. They may be substituted with aliphatic or cyclic hydrocarbon radicals or hetero-substituted with the various substituents defined herein.

The alkynyl groups described herein are preferably lower alkynyl containing from two to six carbon atoms in the principal chain and up to 20 carbon atoms. They may be straight or branched chain and include ethynyl, propynyl, butynyl, isobutynyl, hexynyl, and the like. They may be substituted with aliphatic or cyclic hydrocarbon radicals or hetero-substituted with the various substituents defined herein.

The aryl moieties described herein contain from 6 to 20 carbon atoms and include phenyl. They may be hydrocarbon or heterosubstituted with the various substituents defined herein. Phenyl is the more preferred aryl.

The heteroaryl moieties described are heterocyclic compounds or radicals which are analogous to aromatic compounds or radicals and which contain a total of 5 to 20 atoms, usually 5 or 6 ring atoms, and at least one atom other than carbon, such as furyl, thienyl, pyridyl and the like. The heteroaryl moieties may be substituted with hydrocarbon, heterosubstituted hydrocarbon or hetero-atom containing substituents with the hetero-atoms being selected from the group consisting of nitrogen, oxygen, silicon, phosphorous, boron, sulfur, and halogens. These substituents include lower alkoxy such as methoxy, ethoxy, butoxy; halogen such as chloro or fluoro; ethers; acetals; ketals; esters; heteroaryl such as furyl or thienyl; alkanoxy; hydroxy; protected hydroxy; acyl; acyloxy; nitro; amino; and amido.

The heterosubstituted hydrocarbon moieties described herein are hydrocarbon moieties which are substituted with at least one atom other than carbon, including moieties in which a carbon chain atom is substituted with a hetero atom such as nitrogen, oxygen, silicon, phosphorous, boron, sulfur, or a halogen atom. These substituents include lower alkoxy such as methoxy, ethoxy, butoxy; halogen such as chloro or fluoro; ethers; acetals; ketals; esters; heteroaryl such as furyl or thienyl; alkanoxy; hydroxy; protected hydroxy; acyl; acyloxy; nitro; amino; and amido.

The acyl moieties described herein contain hydrocarbon, substituted hydrocarbon or heteroaryl moieties.

The alkoxycarbonyloxy moieties described herein comprise lower hydrocarbon or substituted hydrocarbon moieties.

The following example illustrates the invention.

EXAMPLES (−)-(1S)-Camphor (2). To a vigorously stirred solution of 600 g (3.89 mol) of (−)-borneol in 1.5 L of glacial acetic acid at 0° C. was added 7.5 L of household bleach (Chlorox™) over a period of 1 h. After 30 min the solid (800 g) was collected by filtration and dissolved in 2 L of hexane. The solution was washed with saturated aqueous $NaHCO_3$ and brine, dried over $Na_2SO_4$ and concentrated to give 570 g (96%) of camphor.

2: mp: 178–180° C.; $[\alpha]_D^{25}$=−39 (c=3.0, EtOH), $^1$H NMR see Table; $^{13}$C NMR (100 MHz, $CDCl_{13}$) δ (ppm): 9.20, 19.10, 19.74, 27.02, 29.90, 43.05, 43.25, 46.73, 57.64, 219.46.

500 MHz $^1$H NMR Data in $CDCl_3$ for Camphor (2)

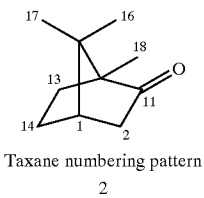

Taxane numbering pattern
2

| Proton | δ (ppm) | J (Hz) | n.O.e. (%) |
|---|---|---|---|
| 1β | 2.09 | 4.6 (2β) | 2β (1.0) |
| | | 3.6 (14β) | |
| 2α | 1.85 | 17.4 (2β) | 2β (6.5) |
| 2β | 2.35 | 17.4 (2α) | 1β (0.9); 2α (5.7); 16 (1.2) |
| | | 3.6 (1β) | |
| | | 3.1 (14β) | |
| 13α | 1.41 | 12.7 (13β) | 13β (6.8) |
| | | 9.3 (14α) | |
| | | 3.8 (14β) | |
| 13β | 1.68 | 12.7 (13α) | 14β (1.7); 13β (10.9); 17 (1.9); 18 (.7) |
| | | 12.6 (14β) | |
| | | 4.4 (14α) | |
| 14α | 1.34 | 12.3 (14β) | 14β (7.4) |
| | | 9.6 (13α) | |
| | | 4.4 (13β) | |
| 14β | 1.96 | 12.3 (14α) | 13β (0.8); 14α (9.6); 17 (1.3) |
| | | 12.6 (13β) | |
| | | 3.8 (13α) | |
| | | 3.6 (1β) | |
| | | 3.1 (2β) | |
| 16 | 0.84 | s | 2β (1.0); 1β (0.6) |
| 17 | 0.97 | s | 1β (0.1); 14β (0.5); 13β (0.4) |
| 18 | 0.92 | s | 13β (0.4) |

(+)-Camphorquinone (3). To a solution of 370 g (2.43 mol) of (−)-camphor in 300 mL of acetic anhydride at 25° C. was added 500 g (4.5 mol) of $SeO_2$. The solution was heated to reflux at 150° C. with vigorous mechanical stirring for 4 h, then filtered through coarse filter paper. The residue was washed with ten 200 mL portions of ethyl acetate. The ethyl acetate solution was combined with the acetic anhydride filtrate and concentrated to a volume of 500 mL. The solution was cooled to 0° C. to give a bright yellow solid which was collected by filtration. The filtrate was concentrated to a volume of 300 mL and cooled to give a second batch of yellow product. The remaining residue was cooled to −10° C., 15% NaOH was added until the solution was basic, and the solution was extracted with two 1 L portions of ethyl acetate. The collected yellow product was dissolved in ethyl acetate extract and the solution was washed with saturated aqueous $NaHCO_3$ and brine, dried over $Na_2SO_4$ and concentrated to give 378 g (94%) of camphorquinone (3).

3: mp: 210–203° C.; $[\alpha]_D^{25}$=+95.8 (c=4.0, toluene); $^1$H NMR (400 MHz,$CDCl_3$) δ (ppm): 0.94(s, 3H), 1.06(s, 3H), 1.11(s, 3H), 1.64(m, 2H), 1.91(m, 1H), 2.17(m, 1H), 2.62(d, 5.2). $^{13}$C NMR(100 MHz, $CDCl_3$) δ (ppm): 8.71, 17.37, 21.05, 22.25, 29.91, 42.54, 57.96, 58.62, 202.79, 204.77.

Diol 4. To 800 mL of a 1.0M solution of vinylmagnesium bromide in THF at 0° C. was added a solution of 60 g (0.36 mol) of (+)-camphorquinone (3) in 360 mL of THF. The mixture was warmed to 25° C., and after 12 h 10 mL of deionized water was added dropwise. After 5 min, 10 mL of 5% HCl was added dropwise. The solution was diluted with 1 L of ethyl acetate, the organic layer was separated, washed with saturated aqueous $NaHCO_3$ and brine, dried over $Na_2SO_4$ and concentrated to give a brown solid. The solid was recrystallized from hexane at −78° C. to give 60.5 g of diol 4. The mother liquor was purified by chromatography to yield an additional 12 g of the diol. The total yield was 72.5 g (91%).

4: mp: 84–85° C.; $[\alpha]_D^{25}$=+12 (c=1.4, $CHCl_3$); $^1$H NMR (500 MHz, $CDCl_3$) δ (ppm): see Table; $^{13}$C NMR (100 MHz, $CDCl_3$) δ (ppm) 10.06, 22.49, 23.00, 23.13, 30.45, 49.46, 54.32, 56.26, 83.56, 85.23, 114.40, 114.71, 140.56, 141.39; IR ($CHCl_3$), ν ($cm^{-1}$): 3607, 3550, 3090, 1620; Mass Spec. (CI) 223.6 ($M^+$+1), 205.4.

500 MHz $^1$H NMR Data in $CDCl_3$ for Diol 4

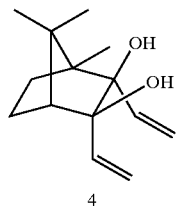

4

| Proton | δ (ppm) | J (Hz) | n.O.e. (%) |
|---|---|---|---|
| 3 | 6.25 | 16.6 (8β) | 10α (0.65); 8α (3.5); 14α (4.7) |
| | | 10.2 (8α) | |
| 10α | 6.15 | 16.6 (9β) | 3α (1.1); 9α (4.4); 13α (7.1) |
| | | 10.2 (9α) | |
| 9β | 5.38 | 16.6 (10α) | 8α + 9α (10.1); |
| | | | 3OH + 11OH (1.3) |
| | | 1.6 (9α) | |
| 8β | 5.36 | 16.6 (3α) | |
| | | 1.6 (8α) | |
| 8α | 5.19 | 10.2 (3α) | 3α + 10α (2.8); 8β + 9β (10.9) |
| | | 1.6 (8β) | |
| 9α | 5.19 | 10.2 | |
| | | 1.6 | |
| OH | 2.73 | | 8β + 9β (2.1); 16 (4.2) |
| OH | 2.68 | | |
| 1β | 1.84 | 4.7 (14b) | 8β (0.5); 14β (2.62); 16 (0.8); 17 (1.1) |
| 14β | 1.67 | 14.2 | 1 (1.8); 14α (10.6); 13β (1.1); 17 (5.5) |
| | | 12.5 | |
| | | 4.7 | |
| | | 3.1 | |
| 14α | 1.56 | m | 3α (2.8); 8α (0.7); 1β (1.0); 14β (2.1); |
| 13α | 1.52 | m | 10α (7.1); 13β (10.6) |
| 13β & Me16 | 1.36 | m | 1β (1.5); 14β (2.4); 13α (41); 17 (2.6); 18 (1.5) |
| Me17 | 0.91 | | 1β (1.0); 14β (2); 13β + 16 (3.9) |
| Me18 | 0.82 | | 10α (1.2); 9β (0.3); 11OH (0.4); 13β + 16 (2.1) |

Ketone 5. To a suspension of 20 g (0.5 mol) of KH in 400 mL of THF at −78° C. was added a solution of 43 g (0.19 mol) of diol 4 in 300 mL of THF. After 2 h 39 mL (0.23 mol) of triethylsilyl chloride was added. After two additional hours the solution was warmed to 25° C. After 8 h 50 ml of deionized H₂O was added dropwise. After 1 h, the solution was partitioned between 1 L of hexane and 200 mL of deionized H₂O. The organic layer was separated, washed with two 100 mL portions of of brine, dried over Na₂SO₄, and concentrated to give a solid mass. The solid was repeatedly recrystallized from hexanes at −78° C. to give 35 g of enone 5. The mother liquor was purified by flash chromatography eluting with 10% ethyl acetate in hexanes to give an additional 3 g of 5. The combined yield of 5 was 38 g (96%).

5: mp 95–97° C.; $[\alpha]_D^{25}$=−7 (c=4.25, CHCl₃); ¹H NMR (500 MHz, CDCl₃), see Table; ¹³C NMR(100 MHz, CDCl₃) δ (ppm) 15.1, 18.9, 21.9, 23.2, 23.9, 28.7, 33.9, 35.9, 49.3, 51.4, 62.0, 135.4, 172.4, 201.3; Mass Spec. (CI) 205.4 (M⁺+1).

500 MHz ¹H NMR Data in CDCl3 for Enone 5

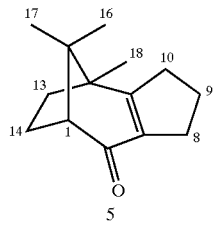

| Proton | δ (ppm) | J (Hz) | n.O.e. (%) |
|---|---|---|---|
| 1β | 2.43 | 7.5 (14β) | 14β (1.9); 17 (2.5); 16 (0.8) |
| 10β + 10α + 8α | 2.56 | m | 18 (1.5); 9α + 9β (3.0) |
| 8β | 2.48 | m | 9α + 9β (5.2) |
| 9α + 9β | 1.93 | m | 10β + 10α + 8α (4.4); 8β (2,6) |
| 13β | 1.87 | 12.5 (13α) 10.4 (13β) 2.9 (14α) | 14β (0.4); 13α (10.3); 18 (1.3); 17 (1.8) |
| 13α | 1.60 | 12.5 (13β) 11.5 (14α) 3.2 (13α) | 10α (0.5); 13β (15.2); 14α (3.4); 18 (0.8) |
| 14β | 2.18 | 12.7 (14β) 10.4 (13β) 3.2 (13α) | 1β (4.0); 13β (3.5); 14α (18.0); 7.5 (1β) 17 (2.2); 16 (1.0) |
| 14α | 1.40 | 12.7 (14β) 11.5 (13α) 2.9 (13β) | 1β (1.7); 14β (16.8); 13α (1.4) |
| Me18 | 1.11 |  | 10β (2.3); 13β (1.1); 13α (0.3) |
| Me17 | 0.93 |  | 1β (1.7); 14β (1.1), 13β (1.4); 18 (0.6); 16 (1.0) |
| Me16 | 0.87 |  | 9β (0.3); 1b (0.7); 18 (0.9); 17 (0.2) |

Ketone 7. To a solution of 2.0 g (9.8 mmol) of enone 5 in 150 mL of THF(150 ml) at 0° C. was added 2 g (10 mmol) of KHMDS. After 1 h the solution was cooled to −78° C. and a solution of 3.8 g (14.5 mmol) of N-phenylsulfonyl phenyloxaziridine in 150 mL of THF was added. After 2 h the mixture was warmed to 25° C. and partitioned between 200 mL of ethyl acetate and saturated aqueous NaHCO₃. The organic layer was separated, washed with brine, dried over Na₂SO₄ and concentrated to give a solid mass. The crude product was purified by chromatography with 20% ethyl acetate in hexanes to give 1.52 g (6.9 mmol, 70% yield) of 7 as an oil.

7: mp 70–71° C.; $[\alpha]_D^{25}$=−14.1; ¹H NMR (400 MHz, CDl₃); δ (ppm): 0.64 (s 3H); 0.97 (s, 3H); 1.15(s, 3H); 1.79 (s, 1H), 1.88 (m, 1H), 1.99 (m, 1H), 2.07(m, 3H), 2.19 (m, 1H), 2.22 (ddd, J=16.4, 8.4, 3.3, 1H), 2.43(d, J=7.7, 1H), 2.58 (m, J=8.5,2.2, 1H), 5.69 (dd, J−3.3, 2.2, 1H); ¹³C NMR (100 MHz, CDCl₃) δ (ppm): 16.79, 21.03, 23.03, 25.12, 28.13, 34.06, 35.99, 46.89, 47.60, 62.53, 85.63, 127.72, 151.56, 212.72.

Epoxy alcohol 8. To a solution of 1.0 g (4.5 mmol) of hydroxyketone 7 in 50 mL of hexane at 25° C. was added 1.8 g (65% purity, 6.8 mmol ) of mCPBA. After 1 h the mixture was diluted with 150 mL of ethyl acetate and 30 mL of 10% aqueous NaS₂O₃ was added. The mixture was then partitioned between 200 mL of ethyl acetate and 150 ml of saturated aqueous NaHCO₃, The organic layer was separated, washed with brine, dried over NaSO₄ and concentrated under vacuum to give 1.05 g (4.44 mmol, 98%) of 8 as a solid.

8: mp 65–67° C.; $[\alpha]_D^{25}$=−83.5 °(c=1.15, CHCl₃); ¹H NMR (500 MHz, CDCl₃), see Table; ¹³C NMR (100 MHz, CDCl₃) δ (ppm): 13.91, 20.21, 23.07, 24.40, 24.87, 33.01, 34.32, 45.33, 45.62, 61.84, 66.86, 75.75, 82.75, 208.43.

400 MHz ¹H NMR Data for Epoxide 8

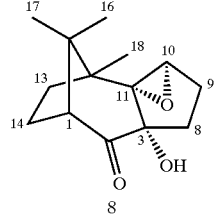

| Proton | δ (ppm) | J (Hz) | n.O.e. (%) |
|---|---|---|---|
| 1β | 2.52 | 7.3 (14β) | 14β (1.1); 17 (0.8) |
| 8α | 2.71 | 14.9 (8β) 11.4 (9β) 4.5 (9α) | 9α (−0.3); 9β (2.1); 8β (11.2) |
| 8β | 1.58 | 14.9 (8α) 9.4 (9α) 5.9 (9β) | 8α (39.4); 9β (0.9) |
| 9α | 2.11 | 15.0 (9β) 9.4 (8β) 4.5 (8α) | 10β (1.1); 9β (11.2); 13β (2.1) |
| 9β | 1.70 | 15.0 (9α) 11.4 (8α) 5.9 (8β) 2.3 (10β) | 10β (1.2); 8α (2.8); 9α (9.7); |
| 10β | 3.55 | 2.3 (9β) | 9α (0.9); 9β (2.0); 18 (3.6); 16 (0.4) |
| 13α | 2.35 | 12.9 (13β) 9.2 (14α) 4.5 (14β) | 14α (0.9); 13β (12.6) |
| 13β | 1.75 | 15.0 (14β) 12.9 (13α) 4.2 (14α) | 13α (11.0); 14β (3.9); 172.1); 18 (0.4) |
| 14α | 2.26 | 13.2 (14β) 9.2 (13α) 4.2 (13β) | 14β (9.8) |
| 14β | 2.01 | 15.0 (13β) 13.2 (14α) 7.3 (1β) 4.5 (13α) | 1β (2.8); 14α (12.0); 13β (2.7); 172.3) |
| 16 | 0.78 |  | 10β (0.6); 8β (0.6); 1β (0.8); 9β (1.2); 17 (1.5) |
| 17 | 0.99 |  | 1β (1.4); 14β (1.3); 13β (1.1); 18 (1.0); 16 (1.3) |
| 18 | 0.82 |  | 10b (2.0); 13b (1.2); 17 (1.3) |

Epoxide 9 (P₂=H). To a solution of 4.52 g (20.5 mmol) of hydroxyketone 7 in 150 mL of methanol at 0° C. was added 1.55 g (41.0 mmol) of NaBH₄. After 1 h 25 mL of 1M NaOH solution was added. The mixture was diluted with 200 ml of ethyl acetate. The organic layer was washed with water, saturated aqueous ammonium chloride, saturated aqueous NaHCO$_3$ and brine, dried over Na$_2$SO$_4$ and concentrated to give 4.53 g (19 mmol, 100%) of epoxide 9 (P$_2$=H) as a white solid.

9 (P$_2$=H): mp 122–124; [α]$_D^{25}$=+28 (c=1.7, MeOH); $^1$H NMR(500 MHz, CDCl$_3$), see Table; $^{13}$C NMR (100 MHz, CDCl$_3$) δ (ppm): 13.38, 20.92, 24.41, 25.09, 25.95, 32.12, 35.48, 44.22, 45.25, 52.28, 65.70, 74.32, 78.15, 81.43. MW=238.33, Analysis Calc. for C$_{14}$H$_{22}$O$_3$ C:70.56, H:9.30; Found C:70.64, H:9.32.

centrated for azeotropic removal of excess pyridine to give 0.73 g (3.06 mmol, 99%) of alkene 10 (P$_2$=P$_{10}$=H) as a white powder.

10 (P$_2$=P$_{10}$=H): mp 212–215° C.; [α]$_D^{25}$=+59.9 (c=3.7, MeOH); $^1$H NMR (500 MHz, CDCl$_3$), see Table; $^{13}$C NMR (100 MHz, CDCl$_3$) δ (ppm): 23.31, 26.26, 27.58, 31.13, 32.51, 38.34, 43.33, 53.21, 67.93, 75.72, 89.66, 99.74, 123.72, 141.12. ; Mass spec. (CI) 354 (M+1, 100), 336 (44), 317 (26) 222 (25), 204 (50); MW=238.33, Analysis Calc. for C$_{14}$H$_{22}$O$_3$ C:70.56, H:9.30; Found C:70.26, H:9.13.

500 MHz $^1$H NMR Data in CDCl$_3$ for Epoxide 9 (P$_2$ = H)

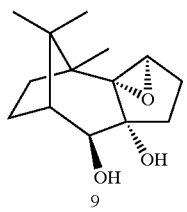

9

| Proton | δ (ppm) | J (Hz) | n.O.e. (%) |
|---|---|---|---|
| 1β | 1.95 | 7.7 (14β); 2.8 (2β) | 2α (1.8); 17 (0.9) |
| 2α | 3.85 | 2.8 (1β) | 1β (0.4); 14α (0.7) |
| 8α | 1.35 | 14.1 (8β); 8.6 (9α); 3.9 (9β) | 8β (11.9); 9α (1.2) |
| 8β | 2.56 | 14.1 (8α); 5.3 (9β); 2.1 (9α) | 9β (1.0); 8α (11.7); |
| 9α | 2.07 | 14.6 (9β); 8.6 (8α); 2.1 (8β) | 9β (12.8); 8α (1.6) |
| 9β | 1.76 | 14.6 (9α); 5.3 (8β); 3.9 (8α); 1.9 (10β) | 10β (0.9); 8β (0.9); 9α (10.2) |
| 10β | 3.48 | 1.3 (9β) | 9β (1.0); 18 (1.2) |
| 13α | 2.18 | 16.8 (14α); 13.3 (13β); 8.0 (14β) | 13β (2.6) |
| 13β | 1.49 | 13.3 (13α); 9.6; 4.4 | 13α (6.2); 17 (0.6); 18 (0.5) |
| 14α | 1.83 | m | |
| 14β | 1.89 | m | |
| 16 | 1.05 | s | 10β (0.5); 17 (0.6); 18 (1.4) |
| 17 | 0.92 | s | 1β (0.6); 14β (0.5); 13β (0.8); 18 (0.3) |
| 18 | 0.73 | s | 10β (1.0); 13β (0.6); 16 (0.4); 17 (0.7) |

500 MHz $^1$H NMR Data in CDCl$_3$ for Alkene 10 (P$_2$ = P$_{10}$ = H)

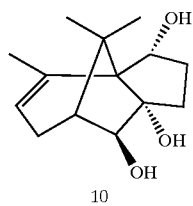

10

| Proton | δ (ppm) | J (Hz) | n.O.e. (%) |
|---|---|---|---|
| 1β | 1.66 | 5.6 (14β) | 2α (4.0); 14β (2.1); 16 (1.6); 17 (0.3) |
| 2β | 3.83 | s | OH (2.3); 14α (2.9); OH (2.4); 1β (1.9); OH (3.9) |
| 8α | 1.80 | 12.2 (8β); 7.7 (9α); 3.5 (9β) | 2α (2.2); 8β (16.2); 9α (3.3) |
| 8β | 2.26 | 12.2 (8α); 8.3 (9α); 3.9 (9β) | 10β (1.3); 8α (14.9); 16 (4.1) |
| 9α | 2.10 | 12.1 (9β); 8.6 (8β); 7.7 (9α); 5.9 (10β) | 10β (0.5); 9β (13.4); 8α (1.7) |
| 9β | 2.34 | 12.1 (9α); 5.6 (10β); 3.9 (8β); 3.5 (8α) | 10β (2.5); 9α (12.5); 8β (0.7); 16 (1.5) |
| 10β | 4.46 | 5.9 (9α); 5.6 (9β) | 9β (2.3); 8β (0.5); 16 (3.7); 17 (0.7) |
| 13 | 5.49 | m | 14β (1.9); 14α + 18 (4.7) |
| 14α | 2.02 | 17.9 (14β) | 13 (1.9); 2α (4.4); 14β (13.8) |
| 14β | 2.43 | 17.9 (14α); 5.6 (1β); 1.7 (18) | 13 (2.5); 14α + 18 (17.1); 1β (3.1); 17 (2.6) |
| 16 | 1.19 | s | 10β (3.7); 9β (1.6); 8β (3.5); 1β (2.8); 17 (0.8) |
| 17 | 1.05 | s | 13 (0.1); 10β (0.6); 14β (1.4); 1β (0.8); 16 (1.1) |
| 18 | 2.01 | 1.3 (13); 1.7 (14β) | 13 (2.9) |

Alkene 10 (P$_2$=P$_{10}$=H). To a solution of 0.74 g (3.1 mmol) of epoxide 9 (P$_2$=H) in 50 mL of dichloromethane at −78° C. was added 4.5 mL (31 mmol) of triethylamine and 1.9 mL (10 mmol) of TMSOTf in that order. The mixture was warmed to −30° C. and after 2 h 2 mL of anhydrous MeOH was added. After 10 min the mixture was concentrated and to the residue was added 10 mL of acetonitrile, 10 mL (124 mmol) of pyridine, and 3 mL (86.7 mmol) of aqueous HF. This mixture was stirred at 25° C. for 5 h and diluted with 150 mL of ethyl acetate. The solution was washed twice with 100 mL of saturated aqueous NaHCO$_3$ and brine. The aqueous layers were combined and extracted twice with 100 mL of ethyl acetate. The organic layers were combined, washed with brine, dried over Na$_2$SO$_4$ and concentrated. The residue was diluted with 150 mL of hexane and con- Alkene 10 (P$_2$=H, P$_{10}$=TES). To a solution of 0.7 g (2.94 mmol) of triol 188 in 5 mL of dichloromethane at 25° C. was added 1.2 mL (8.6 mmol) of triethylamine and 0.5 mL (2.92 mmol) of triethylsilyl chloride. After 10 h 0.3 mL (1.7 mmol) of triethylsilyl chloride and 1 mL (7.2 mmol) of triethylamine were added. After 1 h 0.06 mL (1.6 mmol) of anhydrous methanol was added. After 10 min reaction mixture was diluted with 150 mL of ethyl acetate, washed with saturated aqueous NaHCO$_3$ and brine, dried over Na$_2$SO$_4$ and concentrated to give 1.03 g (2.92 mmol, 99%) of alkene 10 (P$_2$=H, P$_{10}$=TES).

10 (P$_2$=H, P$_{10}$=TES): [α]$_D^{25}$= (c=, MeOH); $^1$H NMR (500 MHz, CDCl$_3$); $^{13}$C NMR (100 MHz, CDCl$_3$) δ (ppm): 4.92, 6.84, 23.44, 25.42, 27.75, 31.02, 32.10, 38.73, 43.62, 53.43, 66.82, 74.22, 89.20, 98.46, 122.23, 142.38. ;

MW=238.33, Analysis Calc. for $C_{20}H_{36}O_3Si$, C:68.13, H: 10.29; Found: C:68.15, H: 10.21.

Alcohol 11. To a cooled solution of 23.11 g (98 mmol) of iodine in 250 ml of THF (45° C.) was added by small portions 14.74 g (98 mmol) of Samarium, the mixture was stirred for 30 min (yellow solid: $SmI_3$) then 15 min at room temperature. The enone 5 (10 g, 49 mmol) was added as a solid and the resulting mixture was stirred for 30 min.3.7 g (98 mmol) of $NaBH_4$.was added by small portions at −20° C. After 3 h, the mixture was poured into a mixture of 10 g of $NaHCO_3$ and 50 ml of a saturated aqueous solution of $Na_2S_2O_3$ and stirred for 1 h. The mixture was diluted by 100 ml of AcOEt, filtered through a cake of celite and concentrated to lead to a mixture of the β-allylic alcohol (20%) and the α-allylic alcohol 11 (80%) as a colorless oil. $^1$H NMR (400 MHz, $CDCl_3$), δ (ppm): 0.87 (s, 3H, 16Me), 0.90 (s, 3H, 17Me), 0.91 (s, 3H, 18Me), 1.34 (d, 1H), 1.60 (m, 4H), 1.81 (m, 3H), 2.23 (m, 2H), 2.32 (m, 1H), 2.44 (m, 1H), 4.41 (brs, 1H, H2β).

Epoxide 12 ($P_2$=H). The above crude oil was dissolved in 122 ml of dichloromethane and 368 ml of hexane at −15° C. and $NaHCO_3$ in powder (12.35 g, 147 mmol) was introduced followed by 21.14 g (73.5 mmol) of mCPBA. The reaction mixture was stirred for 2 h30 at 0° C. then filtered. The organic layer was washed by 25 ml of a 1:1 solution of $NaHCO_3$ and $Na_2S_2O_3$, dried over $Na_2SO_4$ and concentrated to give a mixture of unreacted β-allylic alcohol and the desired α-epoxy-alcohol 12 (97%) as a colorless oil.

The crude oil was dissolved in 50 ml of hexane and cooled to −78° C., the crystallized α-epoxy-alcohol 12 was filtered and dryed. 8.5 g (78% over 3 steps) of α-epoxy-alcohol 12 was obtained. m.p. 98–100° C.; $^1$H NMR (500 MHz, $CDCl_3$), δ (ppm): 0.82 (s, 3H, 16Me), 0.87 (s, 3H, 17Me), 1.03 (s, 3H, 18Me), 1.33 (m, J=16.1, 8.3 Hz, 1H, H9α), 1.41 (m, 1H, H13β), 1.42 (m, 1H, H14β), 1.53 (ddd, J=13.3, 5.9, 3 Hz, 1H, H8β), 1.57 (m, 1H, H10β), 1.58 (m, J=5.9 Hz, 1H, H9β), 1.78 (ddd, J=6.8, 5.9, 1.5 Hz, 1H, H1), 1.82 (d, J=9.8 Hz, 1H, 2-OH), 1.90 (m, 1H, H10α), 1.95 (m, 1H, H14α), 1.96 (m, 1H, H13α), 2.21 (dd, J=13.3, 8.3 Hz, 1H, H8α), 4.00 (dd, J=9.8, 5.9 Hz, 1H, H2β).

To the mother liquor was added 21.4 g (244 mmol) of $MnO_2$ at 0° C., the mixture was stirred at 0° C. for 1 h and 2 h at room temperature.The reaction mixture was then filtered through a cake of sea sand and concentrated to afford 2 g (20%) of recovered enone 5.

Epoxide 12 ($P_2$=PMB). A solution of 1 g (4.5 mmol) of the above α-epoxy-alcohol 12 ($P_2$=H) in 10 ml of DMF was added to 500 mg (13.5 mmol) of dry NaH. The resulting mixture was stirred for 30 min then 672 μl (4.95 mmol) of PMBCl was introduced. After 2 h30, the reaction mixture was cooled to −15° C., quenched by addition of 1 ml of methanol then poured into 10 ml of a saturated aqueous solution of $NaHCO_3$ and extracted twice with 50 ml of hexane/ethyl acetate (1:1). The organic layer was washed with 5 ml of brine, dried over $Na_2SO_4$ and concentrated. A flash chromatography (hexane/ethyl acetate 9:1) yielded to 1.496 g (97%) of the epoxide 12 ($P_2$=H). $^1$H NMR (500 MHz, $CDCl_3$), δ (ppm): 0.77 (s, 3H, 16Me), 0.87 (s, 3H, 17Me), 1.02 (s, 3H, 18Me), 1.37 (dd, J=8, 7 Hz, 1H, H9α), 1.39 (dd, J=10, 4.8 Hz, 1H, H13β), 1.45 (dddd, J=13.1, 9.9, 7.7, 3.2 Hz, 1H, H14β), 1.49 (m, 1H, H8β), 1.51 (m, 1H, H10β), 1.55 (m, J=8 Hz, 1H, H9β), 1.85 (dd, J=7.7, 5.8 Hz, 1H, H1), 1.93 (m, J=12.8 Hz, 1H, H10α), 1.93 (dd, J=13.1, 1.9 Hz, 1H, H14α), 1.98 (dd, J=10, 1.9 Hz, 1H, H13α), 2.18 (dd, J=13.4, 7 Hz, 1H, H8α), 3.74 (d, J=5.8 Hz, 1H, H2β), 3.81 (s, 3H, OMe), 4.50 (d, J=11.8 Hz, 1H, Hb), 4.59 (d, J=11.8 Hz, 1H, Ha), 6.87 (d, J=8.7 Hz, 2H, H2'), 7.29 (d, J=8.7 Hz, 2H, H1').

General procedure for synthesis of Epoxides 14 ($P_2$=H or PMB). To a refluxing solution of 1 g (4.5 mmol) of α-epoxide 12 in 123.5 ml of hexane was added 26.5 ml (45 mmol) of a 1.7M solution of tbutyllithium in hexane through the condenser. The resulting mixture was refluxed for 2 h then cooled to −10° C. and 3 ml of methanol was slowly added. The mixture was concentrated, the yellow solid was dissolved in 25 ml of ethyl acetate and 2 ml of water and stirred for 15 min at room temperature. The mixture was dried over $Na_2SO_4$, filtered and the solid was washed twice with 25 ml of ethyl acetate. The combined organic layers were concentrated and the crude 13 was used for the second step without further purification. $^1$H NMR of diol 13 (300 MHz, $CDCl_3$): δ (ppm) 0.64 (s, 3H, 18Me), 0.97 (s, 3H, 16Me), 1.15 (s, 3H, 17Me), 1.42 (ddd, J=14.2, 9.1, 9 Hz, 1H, H8α), 1.53 (m, 1H, H13β), 1.65 (m, 1H, H14β), 1.72 (dddd, J=14.8, 10.1, 9, 1.4 Hz, 1H, H9β), 1.86 (dd, J=6.8, 3.4 Hz, 1H, H1), 2.03 (ddd, J=13.3, 9.4, 4 Hz, 1H, H14α), 2.11 (ddd, J=14.8, 9.1, 2 Hz, 1H, H9α), 2.12 (s, 1H, 3-OH), 2.20 (m, 1H, H13α), 2.20 (ddd, J=14.2, 10.1, 2 Hz, 1H, H8β), 2.91 (d, J=9.4 Hz, 1H, 2-OH), 3.40 (d, J=1.4 Hz, 1H, H10β), 3.76 (dd, J=9.4, 3.4 Hz, 1H, H2β).

The crude was dissolved in 50 ml of dichloromethane and 2.6 g (9 mmol) of mCPBA in 45 ml of dichloromethane were added. After 14 h, the mixture was diluted with 55 ml of dichloromethane and washed with 50 ml of a 1:1 saturated aqueous solution of $NaHCO_3$ and $Na_2S_2O_3$. The aqueous layer was extracted twice with 50 ml of dichloromethane and the combined organic layers were dried over $Na_2SO_4$ and concentrated. Flash chromatography (hexane/ethyl acetate 1:1) afforded the epoxy-alcohol 14 as a colorless oil, yield 59% for $P_2$=H. $^1$H NMR of the 2,3-dihydroxy-epoxide 14 (500 MHz, $CDCl_3$): δ (ppm) 0.72 (s, 3H, 18Me), 0.86 (s, 3H, 16Me), 0.95 (s, 3H, 17Me), 1.42 (ddd, J=14.2, 9.1, 9 Hz, 1H, H8α), 1.53 (m, 1H, H13β), 1.65 (m, 1H, H14β), 1.72 (dddd, J=14.8, 10.1, 9, 1.4 Hz, 1H, H9β), 1.86 (dd, J=6.8, 3.4 Hz, 1H, H1), 2.03 (ddd, J=13.3, 9.4, 4 Hz, 1H, H14α), 2.11 (ddd, J=14.8, 9.1, 2 Hz, 1H, H9α), 2.12 (s, 1H, 3-OH), 2.20 (m, 1H, H13α), 2.20 (ddd, J=14.2, 10.1, 2 Hz, 1H, H8β), 2.91 (d, J=9.4 Hz, 1H, 2-OH), 3.40 (d, J=1.4 Hz, 1H, H10β), 3.76 (dd, J=9.4, 3.4 Hz, 1H, H2β).

Or as a white solid, yield 25% for $P_2$=PMB, m.p. 88–90° C., see NMR below.

Epoxide 14 ($P_2$=PMB). A solution of 1.41 g (5.9 mmol) of the above epoxydiol 14 ($P_2$=H) in 25 ml of DMF was added to 660 mg (17.88 mmol) of dry NaH. The resulting mixture was stirred for 30 min then 808 μl (5.9 mmol) of PMBCl was introduced. After 1 h, the reaction mixture was quenched by addition of 2 ml of methanol and diluted by 100 ml of hexane/ethyl acetate (1:1). The organic layer was washed with 20 ml of water, dried over $Na_2SO_4$ and concentrated. Flash chromatography (hexane/ethyl acetate 8:2) afforded 1.93 g (91%) of product 14 ($P_2$=PMB) as white solid. m.p. 88–90° C.; $^1$H NMR (500 MHz, $CDCl_3$), δ (ppm): 0.72 (s, 3H, 18Me), 0.84 (s, 3H, 16Me), 0.97 (s, 3H, 17Me), 1.50 (ddd, J=13.1, 11.8, 4.1 Hz, 1H, H13β, 1.56 (m, 1H, H8α), 1.58 (m, 1H, H9β), 1.67 (ddd, J=13.3, 7, 4.5 Hz, 1H, H14β), 1.82 (dd, J=13.3, 8.7 Hz, 1H, H8β), 1.99 (dd, J=7, 3.2 Hz, 1H, H1), 2.05 (dd, J=13.1, 8.7 Hz, 1H, H9α), 2.17 (ddd, J=13.3, 9.7, 4. 1 Hz, 1H, H14α), 2.42 (ddd, J=13.1, 9.7, 4.5 Hz, 1H, H13α), 2.89 (s, 1H, 3-OH), 3.25 (d, J=1 Hz, 1H, H10β), 3.50 (d, J=3.2 Hz, 1H, H2β), 3.81 (s, 3H, OMe), 4.44 (dH, J=11.3 Hz, 1H, Hb), 4.63 (d, J=11.3 Hz, 1H, Ha), 6.87 (d, J=8.6 Hz, 2H, H2'), 7.26 (d, J=8.6 Hz, 2H, H1'); $^{13}$C NMR (100 MHz, $CDCl_3$), δ (ppm): 13.4, 19.1, 21.4, 24.5, 24.7, 32.6, 37.3, 43.9, 4416, 47.7, 55.3, 62.4, 70.8, 72.2, 78.4, 79.6, 113.8, 129.5, 130.2, 139.3.

Alkene 15 ($P_2$=PMB, $P_{10}$=H). To a solution of epoxide 12 ($P_2$=PMB) (15.87 g, 46.4 mmol) in 375 ml of dichloromethane and triethylamine (64.5 ml, 464 mmol) at −78° C. was slowly added 25.2 ml (139.2 mmol) of TMSOTf. The reaction mixture was stirred at −35° C. for 14 h. Methanol (20 ml) was added to quench the reaction and the temperature was allowed to rise at 25° C. The volatils were removed under reduced pressure and the residue was partly dissolved in 500 ml of hexane, filtered on celite. The organic layer was concentrated to give 18.7 g of crude material which was used directly in the next step. $^1$H NMR (500 MHz, $CDCl_3$), δ (ppm): 0.10 (s, 9H, 3-TMS), 0.65 (s, 3H, 18Me), 0.91 (s, 3H, 16Me 1.00 (s, 3H, 17Me), 1.53 (m, 1H, H13β), 1.64 (dt, J=13.8, 8.7 Hz, 1H, H8α), 1.78 (m, 1H, H14β), 1.84 (dd, J=6.9, 3.3 Hz, 1H, H1), 1.98 (m, 1H), 2.20 (m, 1H), 2.22 (m, 1H), 2.30 (m, 1H), 2.47 (m, 1H), 3.44 (d, J=2.9 Hz, 1H, H2β) 3.81 (s, 3H, OMe), 4.45 (d, J=11.6 Hz, 1H, Hb), 4.58 (d, J=11.6 Hz, 1H, Ha), 5.34 (dd, J=3.3, 1.8 Hz, 1H, H10β), 6.87 (d, J=8.4 Hz, 2H, H2'), 7.29 (d, J =8.4 Hz, 2H, H1').

To the mixture of 18.7 g of the above crude material in 460 ml of a 1:3 mixture of dichloromethane/hexane at 0° C. were added 17.15 g (69.6 mmol) of mCPBA and 5.85 g (139.2 mmol) of $NaHCO_3$. The reaction mixture was stirred at room temperature for 4 h and filtered. The solid was washed with 50 ml of hexane and the organic layer was washed twice with 50 ml of a 1:1 aqueous solution of saturated $NaHCO_3$ and saturated $Na_2S_2O_3$, dried over $Na_2SO_4$ and concentrated to lead to 20.2 g of a colorless oil.

To a solution of 20.2 g of the above crude oil in 375 ml of dichloromethane and 64.5 ml (464 mmol) of triethylamine at −45° C. was slowly added 25.2 ml (139.2 mmol) of TMSOTf. The reaction mixture was then stirred at −25° C. for 3 h. Methanol (20 ml) was added to quench the reaction and the temperature was allowed to rise at room temperature. The volatils were removed under reduced pressure and the residue was partly dissolved in 500 ml of hexane, filtered on celite. The organic layer was concentrated to give 20 g of crude product. Crystallization in acetonitrile at −10° C. gave 18 g of a white solid. m.p. 98–100° C.; $^1$H NMR (400 MHz, $C_6D_6$), δ (ppm): 0.13 (s, 9H, $CH_3$ 10-TMS), 0.24 (s, 9H, $CH_3$ 3-TMS), 0.94 (s, 3H, 16Me), 1.27 (s, 3H, 17Me), 1.33 (dt, J=13, 5.6 Hz, 1H, H8β), 1.83 (br t, J=5.2 Hz, 1H, H1), 2.12 (dd, J=13, 6.3 Hz, 1H, H8α), 1.98 (ddd, J=11.7, 6.3, 5.6 Hz, 1H, H9α), 2.03 (ddq, J=17.5, 3.1, 2.3 Hz, 1H, H14β), 2.21 (dt, J=2.3, 2, 2 Hz, 3H, 18Me), 2.33 (m, 2H, H9β-H14α), 3.28 (s, 3H, OMe), 3.70 (dd, J=5.2, 0.6 Hz, 1H, H2β), 4.10 (d, J=10.8 Hz, 1H, Hb), 4.23 (d, J=10.8 Hz, 1H, Ha), 4.40 (dd, J=10.5, 6.3 Hz, 1H, H10β), 5.34 (m, 1H, H13), 6.80 (d, J=8.6 Hz, 2H, H2'), 7.22 (d, J=8.6 Hz, 2H, H1').

To a solution of 18 g of the above solid in 50 ml of acetonitrile and 20 ml of pyridine was added 30 ml of a 48% aqueous solution of HF at 0° C. The mixture was stirred at room temperature for 5 h, poured into a solution of 50 ml of ethyl acetate and $NaHCO_3$ solid was added till no reaction was observed. After filtration, the volatils were removed under reduced pressure and a plug chromatography (hexane/ ethyl acetate 1:1) yielded to 12.57 g (75% over 4 steps) of alkene 15 ($P_2$=PMB, $P_{10}$=H) as an oil. $^1$H NMR (500 MHz, $CDCl_3$), δ (ppm): 1.04 (s, 3H, 16Me), 1.13 (s, 3H, 17Me), 1.47 (d, J=7.7 Hz, 1H, 10-OH), 1.68 (dddd, J=15, 7.7, 2.2, 1.9 Hz, 1H, H8β), 1.96 (m, 1H, H1), 1.97 (dt, J=2.2, 1.6, 1.6 Hz, 3H, 18Me), 2.01 (ddq, J=17.9, 2.9, 2.2 Hz, 1H, H14β), 2.10 (dt, J=11.5, 7.7, 7.7 Hz, 1H, H9α), 2.12 (m, J=2.2 Hz, 1H, H8α), 2.25 (ddt, J=11.5, 6, 2.2, 2.2 Hz, 1H, H9β), 2.39 (ddq, J=17.9, 2.9, 1.6 Hz, 1H, H14α), 3.15 (d, J=1.9 Hz, 1H, 3-OH), 3.81 (s, 3H, OMe), 3.82 (d, J=6.1 Hz, 1H, H2β), 4.34 (d, J=11.2 Hz, 1H, Hb), 4.42 (td, J=7.7, 7.7, 6 Hz, 1H, H10β), 4.60 (d, J=11.2 Hz, 1H, Ha), 5.38 (m, J=1.6 Hz, 1H, H13), 6.87 (d, J=8.6 Hz, 2H, H2'), 7.26 (d, J=8.6 Hz, 2H, H1'); $^{13}$C NMR (100 MHz, $CDCl_3$): δ (ppm) 22.3, 25.3, 25.8, 27.9, 38.6, 39.2, 39.7, 50.2, 55.2, 66.1, 72.1, 75.3, 83.4, 90.2, 113.7, 123.4, 129.2, 130.6, 140.5, 159.1.

Ketone 16 ($P_2$=$P_{13}$=H, $P_{10}$=TES): To amethylene chloride (3 ml) solution of alkene 10 ($P_2$=H, $P_{10}$=TES) (0.298 g, 0.845 mmol) at 0° C. was added $Ti(iOPr)_4$ (0.75 ml, 2.53 mmol) and a 2.0 M hexane solution of t-butyl hydroperoxide (1.06 ml, 2.11 mmol) and stirred at 0° C. for 30 min. To the reaction mixture was added dimethylsulfide (0.8 ml, 11 mmol) and stirred at 0° C. for 1 h and warmed to 25° C. for 20 min. The reaction mixture was poured into a flask of THF (40 ml) and stirred vigorously while adding deionized water (0.25 ml) over for 15 min to form a white precipitate. The solution was dried over $MgSO_4$ and filtered through a bed of celite and concentrated. To a methylene chloride (10 ml) solution of the crude reaction mixture was added flash silica gel (1 g) and the mixture was heated under reflux with a 60° C. silicon oil bath for 3 h. The reaction mixture was filtered through a fritted funnel and washed with ethyl acetate and concentrated to give ketone 16 ($P_2$=$P_{13}$=H, $P_{10}$=TES) (0.31 g, 0.841 mmol, 99%) as a white solid.

16 ($P_2$=$P_{13}$=H, $P_{10}$=TES): m: 111–112° C.; $[\alpha]_D^{25}$= (c=, MeOH); $^{13}$C NMR (100 MHz, $CDCl_3$) δ (ppm): 4.87, 6.83, 13.15, 27.29, 33.06, 34.79, 36.47, 37.38, 39.01, 53.18, 69.64, 76.10, 138.35, 157.86, 200.12, 215.95.

500 MHz $^1$H NMR Data in $CDCl_3$ for Ketone 16
($P_2$ = $P_{13}$ = H, $P_{10}$ = TES)

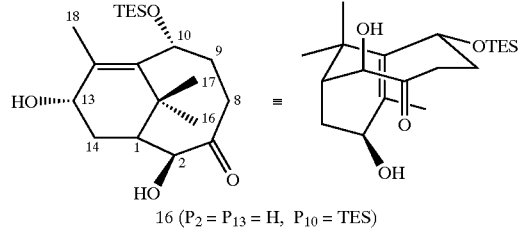

16 ($P_2$ = $P_{13}$ = H, $P_{10}$ = TES)

| Proton | δ (ppm) | J (Hz) | n.O.e. (%) |
|---|---|---|---|
| 1β | 1.94 | 8.0 (14β) | 2α (3.1); 14β (1.8); 16 (0.4); 17 (1.4) |
| | | 1.92 (2α) | |
| 2α | 4.10 | 1.92 (1β) | 13OH (1.6); 2OH (3.8); 1β (4.0); 14α (6.0) |
| 8α | 1.82 | 13.9 (8β) | 8β (19.6); 9α (4.2) |
| | | 5.3 (9β) | |
| 8β | 3.35 | 13.9 (8α) | 10β (3.5); 8α (27.9); 16 (6.9) |
| | | 12.1 (9α) | |
| | | 2.8 (9β) | |
| 9α | 2.57 | 12.1 (8β) | 9β + 18 (15.2) |
| | | 10.4 (10β) | |
| 9β | 1.97 | m | 10β (3.5); 9α (18.5) |

-continued

500 MHz $^1$H NMR Data in CDCl$_3$ for Ketone 16
($P_2 = P_{13}$ = H, $P_{10}$ = TES)

16 ($P_2 = P_{13}$ = H, $P_{10}$ = TES)

| Proton | δ (ppm) | J (Hz) | n.O.e. (%) |
|---|---|---|---|
| 10β | 4.58 | 10.4 (9α) | 8β (1.6); 9β (3.5); 16 (6.5) |
|  |  | 5.3 (9β) |  |
| 13β | 3.98 | 11.8 (14β) | 14β (3.9); 13OH (1.0); 18 (2.3); 17 (3.6) |
|  |  | 9.5 (13OH) |  |
| 14α | 1.75 | 15.9 (14β) | 2α (9.7); 14β (18.7); |
| 14β | 2.91 | 15.9 (14α) | 13β (8.8); 1β (5.1); 14β (24.7); 17 (5.3) |
|  |  | 11.8 (13β) |  |
|  |  | 8.0 (1β) |  |
| 16 | 1.53 | s | 10β (3.8); 8β (1.8); 1β (1.3); 17 (1.4) |
| 17 | 1.02 | s | 13β (2.6); 14β (2.8); 1β (1.6); 16 (1.4) |
| 18 | 1.96 | s |  |
| CH$_3$-TES | 0.95 | 7.9 |  |
| CH$_2$-TES | 0.59 | 7.9 |  |

Ketone 17 ($P_2=P_{13}$=H, $P_{10}$=TES) by epoxy-alcohol fragmentation of 10 ($P_2$=H, $P_{10}$=TES): To a methylene chloride (0.5 ml) solution of alkene 10 ($P_2$=H, $P_{10}$=TES) (50 mg, 0.142 mmol) at 0° C. was added Ti(iOPr)$_4$ (0.17 ml, 0.57 mmol) and a 2.0 M hexane solution of t-butyl hydroperoxide and stirred at 0° C. for 30 min. To the reaction mixture was added dimethylsulfide (0.17 ml, and stirred at 0° C. for 1 h and warmed to 25° C. for 20 min then heating to reflux with a 60° C. silicon oil bath for 12 h. The reaction mixture was poured into a flask of THF (20 ml) and stirred vigorously while adding deionized water (0.15 ml) over for 15 min to give a white precipitate. The solution was dried over MgSO$_4$ and filtered through a bed of celite and concentrated. Filtration of the reaction mixture through a plug silica gel gave ketone 17 ($P_2=P_{13}$=H, $P_{10}$=TES) (51 mg, 97%) as a white powder.

Ketone 17 ($P_2=P_{13}$=H, $P_{10}$=TES) by epimeriztion of ketone 16 ($P_2=P_{13}$=H, $P_{10}$=TES): To a methylene chloride solution of ketone 16 ($P_2=P_{13}$=H, $P_{10}$=TES) (12 mg, 0.033 mmol)was added Ti(iOPr)$_4$ (0.05 ml, 0.17 mmol) and heated to reflux with a 60° C. silicon oil bath for 6 h. The reaction mixture was poured into a flask of THF (20 ml) and stirred vigorously while adding deionized water (0.05 ml) over for 15 min to give a white precipitate. The solution was dried over MgSO$_4$ (1 g) and filtered through a bed of celite and concentrated. Purification of the reaction mixture by flash silica gel chromatography eluting with 75% ethyl acetate in hexanes gave ketone 17 ($P_2=P_{13}$=H, $P_{10}$=TES) (11 mg, 92%) as a white powder. 195a: mp: 76–80° C.; $[\alpha]_D^{25}$=+ 16.1 (c=1.0, CHCl$_3$).

500 MHz 1H NMR Data in CDCl3 for Ketone 17
($P_2 = P_{13}$ = H, $P_{10}$ = TES)

17 ($P_2 = P_{13}$ = H, $P_{10}$ = TES)

| Proton | δ (ppm) | J (Hz) | n.O.e. (%) |
|---|---|---|---|
| 1β | 2.17 | 6.5 (14β) | 2β (3.5); 14β (3.2); 16 (2.4); 17 (3.3) |
|  |  | 6.0 (2β) |  |
| 2β | 4.52 | 7.6 (2OH) | 2OH (0.8); 8β (2.6); 1β (2.7); 16 (2.9) |
|  |  | 6.0 (1β) |  |
| 2OH | 2.91 | 7.6 (2β) | 2β (2.4); 14α (5.5); 13OH (−4.7) |
| 8α | 2.30 | 12.9 (8β) | 8β (16.7); 9β (4.3); 9α (1.7) |
|  |  | 5.3 (9α) |  |
|  |  | 3.4 (9β) |  |
| 8β | 2.61 | 14.5 (9β) | 10β + 2β (8.8); 8α (24.1); 9β (4.0); 16 (4.0) |
|  |  | 12.9 (8β) |  |
|  |  | 3.0 (9α) |  |
| 9α | 2.49 | 15.7 (9β) | 9β + 18 (25.5) |
|  |  | 5.4 (10α) |  |
|  |  | 5.3 (8α) |  |
|  |  | 3.0 (8β) |  |
| 9β | 1.98 | 15.7 (9α) | 9α (15.5) |
|  |  | 14.5 (8β) |  |
|  |  | 9.0 (10β) |  |
|  |  | 3.4 (8α) |  |
| 10β | 4.53 | 9.0 (9β) | 8β (1.9); 16 (5.6) |
|  |  | 5.4 (9α) |  |
| 13β | 4.04 | 10.9 (13OH) | 14β (3.1); 18 (1.9); 13OH (2.0); 17 (2.9) |
|  |  | 10.4 (14β) |  |
|  |  | 3.0 (14α) |  |
|  |  | 0.7 (18) |  |
| 13OH | 1.81 | 10.9 (13β) | 13β (1.1); 14α + 18 (5.8) |
| 14α | 1.98 | 16.4 (14β) | 2OH (6.3); 14β (18.5); 13OH (2.0) |
|  |  | 3.0 (13β) |  |
| 14β | 2.46 | 16.4 (14α) | 13β (3.5); 1β (2.6); 23.2); 17 (4.8) |
|  |  | 10.4 (13β) |  |
|  |  | 6.5 (1β) |  |
| 16 | 1.49 | s | 10β + 2β (9.5); 8β (2.2); 1β (2.4); 17 (1.9) |
| 17 | 1.12 | s | 13β (2.0); 14β (1.9); 1β (1.5); 16 (1.0) |
| 18 | 1.96 | 0.7 (13β) |  |
| CH$_3$-TES | 0.96 | 7.6 (CH$_2$-TES) |  |
| CH$_2$-TES | 0.60 | 7.6 (CH$_3$-TES) |  |

Ketone 17 ($P_2$=PMB, $P_{13}$=H, $P_{10}$=TES). To a stirred solution of alkene 15 ($P_2$=PMB, $P_{10}$=H) (7.31 g, 20.39 mmol) in methylene chloride (70 ml) and hexanes (70 ml) was added at room temperature buffer solution pH 8 (50 ml), then mCPBA (8.8 g at 60%, 30.6 mmol). After 4 hrs at room temperature, saturated sodium bisulfite solution (50 ml) was added. The white precipitate was filtered through celite. The aqueous layer was extracted with ethyl acetate. The combined organic extracts were washed with saturated sodium bisulfite solution, saturated sodium bicarbonate solution then brine, dried over sodium sulfate and filtered. The solvent was removed under reduced pressure to afford 7.42 g (97%) of crude epoxide as a white solid. The white solid obtained was generally subjected to the next reaction without further purification. A sample from a related experiment was purified via flash chromatography (6:4 Hex-EtOAc). Mp 114° C.; $^1$H (C$_6$D$_6$, 400 MHz, VR-1-257) δ 0.54 (3H, s, 16-Me), 0.67 (3H, s, 17-Me), 1.38 (1H, ddd, J=15.7, 6.8, 4.9 Hz, H$_{14β}$), 1.46 (1H, t, J=6.8 Hz, H$_1$), 1.72 (3H, s, 18-Me), 1.68–1.75 (1H, m, H$_{8β}$), 1.77–1.86 (1H, m, H$_{9β}$, 2.10–2.04 (1H, m, H$_{9α}$), 2.54 (1H, d, J=4.9 Hz, H$_{13}$), 2.56 (1H, d, J=15.7 Hz, H$_{14α}$),2.59–2.51 (1H, m, H$_{8α}$), 3.30 (3H, s, OMe), 3.57 (1H, d, J=6.8 Hz, H$_2$), 3.94 (1H, d, J=4.9 Hz, H$_{10}$), 4.28 and 4.93 (1H, d, J=11.4 Hz, H$_{1'}$), 6.07 (1H, broad s, 3-OH), 6.79 (2H, d, J=8.8 Hz, H$_{4'}$), 7.30 (2H, d, J=8.8 Hz, H$_3$·); $^{13}$C (C$_6$D$_6$, 100 MHz, VR-257) δ 21.9, 22.4, 24.0, 27.4, 35.2, 40.0, 44.8, 49.7, 54.8, 61.0, 65.1, 65.4, 72.2, 77.6, 82.6, 91.2, 114.1, 129.5, 131.4, 159.7; Anal. Calcd. for C$_{22}$H$_{30}$O$_5$: C, 70.56; H, 8.07; Found: C, 70.65; H, 8.20.

To a stirred solution of crude material from the preceeding experiment (7.42 g, 19.8 mmol) in DMF (100 ml) was added at room temperature imidazole (6.74 g, 99.0 mmol) then TESCl (10 ml, 59.4 mmol). The reaction was stirred overnight (16 hrs) then was quenched with MeOH (10 ml). The solvents were removed under reduce pressure. To the residue was added hexanes, then the precipitate formed was filtered through celite. The solvent was removed under reduced pressure and the residue was purified via flash chromatography (9:1 Hex-EtOAc) to afford 9.28 g (93% for two steps) of the epoxide as a colorless oil. $^1$H (C$_6$D$_6$, 500 MHz, VR-1-161-2) δ 0.64 (3H, s, 16-Me), 0.70 (6H, q, J=8.0 Hz, TES), 0.79 (3H, s, 17-Me), 1.09 (9H, t, J=8.0 Hz, TES), 1.45 (1H, ddd, J=15.5, 7.0, 5.0 Hz, H$_{14β}$), 1.54 (1H, t, J=7.0 Hz, H$_1$), 1.59 (3H, s, 18-Me), 1.75–1.81 (1H, m, H$_{8β}$), 1.86–1.94 (1H, m, H$_{9β}$), 1.98–2.03 (1H, m, H$_{9α}$), 2.55 (1H, d, J=5.0 Hz, H$_{13}$), 2.65 (1H, d, J=15.5 Hz, H$_{14α}$), 2.69–2.76 (1H, m, H$_{8α}$), 3.32 (3H, s, OMe),3.64 (1H, d, J=7.0 Hz, H$_2$), 4.25 (1H, d, J=5.0 Hz, H$_{10}$), 4.36 and 5.00 (1H, d, J=11.0 Hz, H$_{1'}$), 5.74 (1H, s, 3-OH), 6.78 (2H, d, J=9.0 Hz, H$_{4'}$), 7.35 (2H, d, J=9.0 Hz, H$_3$·); $^{13}$C (C$_6$D$_6$, 100 MHz, VR-1-262) δ 6.0, 7.3, 21.8, 22.4, 25.2, 27.9, 36.1, 40.0, 45.7, 49.2, 54.7, 61.6, 65.1, 65.6, 72.1, 78.2, 83.9, 91.2, 114.0, 129.6, 131.9, 159.6; Anal. Calcd. for C$_{28}$H$_{44}$O$_5$Si: C, 68.81; H, 9.07; Found: C, 68.58; H, 9.21.

To a solution of the epoxide from the preceeding experiment (310 mg, 634 μmol) in hexanes (6 ml) at room temperature was added titanium isopropoxide (760 μl, 2.54 mmol, 4 eq.). The reaction mixture was allowed to stir at reflux for 45 min. After cooling at room temperature, the reaction was quenched with water (2 ml), then EtOAc (10 ml) was added. The white precipitate was stirred for 1 hr at room temperature, then was filtered through celite and rinsed with EtOAc. The solution was concentrated under reduce pressure to afford 325 mg of crude product as a colorless oil. This oil was generally subjected to the next reaction without further purification. A sample from a related experiment was purified via flash chromatography (8:2 Hex-EtOAc) to afford ketone 17 (P$_2$=PMB, P$_{13}$=H, P$_{10}$=TES) as a white solid. Mp 64° C.; $^1$H (C$_6$D$_6$, 500 MHz, VR-2-130) δ 0.57 (6H, q, J=8.0 Hz, TES), 0.88 (3H, s, 17-Me), 0.98 (9H, t, J=8.0 Hz, TES), 1.04 (3H, s, 16-Me), 1.69 (1H, dddd, J=12.5, 5.0, 5.0, 2.5 Hz, H$_{9β}$), 1.75 (1H, ddd, J=13.0, 5.0, 3.5 Hz, H$_{8α}$), 1.97 (1H, t, J=6.0 Hz, H$_1$), 2.03 (1H, ddd, J=14.0, 13.0, 2.5 Hz, H$_{8β}$), 2.38 (3H, d, J=1.0 Hz, 18-Me), 2.39 (1H, ddd, J=16.0, 10.0, 6.0 Hz, H$_{14β}$), 2.66 (1H, dddd, J=14.0, 12.5, 11.0, 3.5 Hz, H$_{9α}$), 2.74 (1H, dd, J=16.0, 3.0 Hz, H$_{14α}$), 2.85 (1H, d, J=12.0, 13-OH), 3.27 (3H, s, OMe), 4.05 (1H, m, H$_{13}$), 4.06 (1H, d, J=6.0 Hz, H$_2$), 4.32 (1H, dd, J=11.0, 5.0 Hz, H$_{10}$), 4.06 and 4.39 (1H, d, J=11.5 Hz, H$_{1'}$), 6.77 (2H, d, J=8.5 Hz, H$_{4'}$), 7.21 (2H, d, J=8.5 Hz, H$_3$·); $^{13}$C (CDCl$_3$, 100 MHz, VR-1-268) δ 4.8, 6.8, 15.6, 28.1, 28.5, 31.2, 36.4, 36.8, 40.4, 51.8, 55.2, 67.1, 69.1, 70.8, 83.5, 113.8, 129.4, 129.8, 138.2, 140.6, 159.3, 215.9; Anal. Calcd. for C$_{28}$H$_{44}$O$_5$Si: C, 68.81; H, 9.07; Found: C, 68.75; H, 9.14.

Ketone 17 (P$_2$=PMB, P$_{13}$=TBS, P$_{10}$=TES). To a solution of ketone 17 (P$_2$=PMB, P$_{13}$=H, P$_{10}$=TES) (325 mg) in pyridine (6 ml) at −25° C. was added TBSOTf (290 μl, 1.27 mmol, 2 eq.). The mixture was stirred at −20° C. for 4 hrs. The reaction was quenched by addition of MeOH (1 ml), then the solvents were removed under reduce pressure. The white solid was filtered and rinsed with hexanes (8 times). The hexane layer was evaporated to afford an oil who was purified by flash chromatography (9:1 Hex-EtOAc) to afford 377 mg (98% for 2 steps) of ketone 17 (P$_2$=PMB, P$_{13}$=TBS, P$_{10}$=TES) as a colorless oil. $^1$H (C$_6$D$_6$, 500 MHz) δ0.06 (3H, s, DMS), 0.11 (3H, s, DMS), 0.60 (6H, q, J=8.0 Hz, TES), 1.00 (9H, t, J=8.0 Hz, TES), 1.02 (9H, s, tBu), 1.10 (3H, s, 17-Me), 1.18 (3H, s, 16-Me), 1.76 (1H, dddd, J=10.0, 4.4, 4.4, 2.4 Hz, H$_{9β}$), 1.83 (1H, ddd, J=10.4, 4.4, 2.4 Hz, H$_{8α}$), 2.10–2.14 (1H, m, H$_{8β}$), 2.12–2.16 (1H, m, H$_1$), 2.24 (3H, d, J=1.0 Hz, 18-Me), 2.28 (1H, ddd, J=14.5, 9.0, 9.0 Hz, H$_{14β}$), 2.65–2.73 (1H, m, H$_{9α}$), 2.69 (1H, ddd, J=14.5, 7.5, 1.5 Hz, H$_{14α}$), 3.32 (3H, s, OMe),4.12 (1H, d, J=5.0 Hz, H$_2$), 4.11 and 4.44 (1H, d, J=11.5 Hz, H$_{1'}$), 4.37 (1H, dd, J=11.0, 4.50. Hz, H$_{10}$), 4.57 (1H, m, H$_{13}$), 6.79 (2H, d, J=8.5 Hz, H$_{4'}$), 7.23 (2H, d, J=8.5 Hz, H$_3$·); $^{13}$C (CDCl$_3$, 100 MHz, VR-1-269) δ 5.0, −4.3, 4.8, 6.8, 15.2, 18.3, 26.0, 28.1, 28.2, 29.2, 36.8, 36.9, 40.2, 51.9, 55.2, 67.9, 69.4, 70.3, 83.7, 113.7, 129.5, 130.2, 135.0, 143.3, 159.2, 211.2; Anal. Calcd. for C$_{34}$H$_{58}$O$_5$Si$_2$ (VR-1-296): C, 67.72; H, 9.69; Found: C, 67.74; H, 9.61.

Ketone 18 (P$_2$=PMB, P$_{13}$=TBS, P$_{10}$=TES). To a solution of ketone 17 (P$_2$=PMB, P$_{13}$=TBS, P$_{10}$=TES) (200 mg, 332 μmol)in dry THF (16.5 ml) at −5° C. was added KHMDS (3.3 ml at 1 M in THF, 3.3 mmol) dropwise over 10 minutes. The pale yellow solution was stirred at −5° C. for two hours, then was cooled to −78° C. After 30 minutes at this temperature, MeI (205 μl, 3.3 mmol) was added dropwise and the resulting mixture was allowed to stir at −78° C. for 1.5 hours. The reaction was quenched at −78° C. with a saturated NaHCO$_3$ solution (4 ml) then was warmed to room temperature. The mixture was extracted with hexanes. The organic layer was washed with brine then dried over Na$_2$SO$_4$. The solvent was removed under reduced pressure. The oil thus obtained (229 mg) was subjected to flash chromatography (9:1 Hex-EtOAc) to afford 197 mg (96%) of the ketone 18 (P$_2$=PMB, P$_{13}$=TBS, P$_{10}$=TES) as a white solid. Mp. 68° C.; Anal. Calcd. for C$_{35}$H$_{60}$O$_5$Si$_2$ (VR-2-53): C, 68.13; H, 9.80; Found: C, 67.88; H, 9.82. $^1$H NMR (C$_6$D$_6$, 400 MHz, VR-1-246-1) δ 0.08 (3H, s, DMS), 0.15 (3H, s, DMS), 0.60 (6H, q, J=8.0 Hz, TES), 0.83 (3H, d, J=7.6 Hz, 19-Me), 0.99 (9H, t, J=8.0 Hz, TES), 1.03 (3H, s, 17-Me), 1.09 (9H, s, tBu), 1.15 (3H, s, 16-Me), 1.73 (1H, ddd, J=16.0, 3.7, 1.0 Hz, H$_{9α}$), 1.98 (1H, ddd, J=16.0, 13.2, 5.2 Hz, H$_{9β}$), 2.12 (1H, dd, J=8.0, 2.8 Hz, H$_1$), 2.35 (3H, d, J=0.8 Hz, 18-Me), 2.35 (1H, ddd, J=14.8, 10.0, 8.0 Hz, H$_{14β}$), 2.78 (1H, dd, J=14.8, 6.0 Hz, H$_{14α}$), 2.79–2.87 (1H, m, H$_{8α}$), 3.29 (3H, s, OMe), 4.00 (1H, d, J=11.2 Hz, H$_{1'}$), 4.17 (1H, d, J=2.8 Hz, H$_2$), 4.46 (1H, d, J=11.2 Hz, H$_{1'}$), 4.57 (1H, broad d, J=5.2 Hz, H$_{10}$), 4.62 (1H, broad dd, J=10.0, 6.0 Hz, H$_{13}$), 6.79 (2H, d, J=8.8 Hz, H$_{4'}$), 7.27 (2H, d, J=8.8 Hz, H$_3$·); $^{13}$C NMR (CDCl$_3$, 100 MHz, VR-1-265) δ −5.1, −4.3, 4.5, 6.8, 14.4, 18.2, 19.2, 25.8, 26.0, 26.8, 29.0, 36.7, 43.1, 43.7, 54.2, 55.2, 67.4, 69.6, 69.9, 76.1, 113.7, 129.2, 130.4, 136.6, 138.8, 159.5, 209.6;

Ketone 19 (P$_2$=PMB, P$_{13}$=TBS, P$_{10}$=TES, P$_7$=H). To a stirred solution of ketone 18 (P$_2$=PMB, P$_{13}$=TBS, P$_{10}$=TES)

(49 mg, 80 μmol) in THF (2 ml), at room temperature, was added BMDA solution (390 μl at 0.33 M in THF, 127 μmol). The resulting mixture was allowed to stir at room temperature for 2 hrs, then was cooled to −25° C. 4-penten-1-al (15 μl, 127 μmol) was added and the reaction mixture was stirred for 3 hrs, then was treated with $NH_4Cl$ (1 ml). The mixture was extracted with EtOAc. The organic layer was washed with brine and was dried over $Na_2SO_4$. The solution was concentrated under reduce pressure and the crude product was subjected to flash chromatography (9:1 Hex-EtOAc) to afford 35 mg (63%) of the ketone 19 ($P_2$=PMB, $P_{13}$=TBS, $P_{10}$=TES, $P_7$=H) as a colorless oil (mixture of 2 conformers: 85% chair-chair and 15% chair-boat). $^1$H NMR ($C_6D_6$, 400 MHz) δ 0.07 (3H, s, DMS), 0.14 (3H, s, DMS), 0.61 (6H, q, J=8.0 Hz, TES), 1.00 (9H, t, J=8.0 Hz, TES), 1.02 (3H, s, 19-Me), 1.06 (3H, s, 17-Me), 1.07 (9H, s, tBu), 1.26 (3H, s, 16Me), 1.40–1.49 (1H, m, $H_6$), 1.61–1.68 (1H, m, $H_6$), 1.93 (1H, dd, J=14.0, 4.8 Hz, $H_{9β}$), 2.10 (1H, dd, J=8.8, 3.6 Hz, $H_1$), 2.21–2.28 (1H, m, $H_5$), 2.28 (3H, d, J=1.2 Hz, 18-Me), 2.27–2.35 (3H, m, $H_{14β}$), 2.41–2.50 (1H, m, $H_5$), 2.76 (1H, dd, J=14.0, 6.2 Hz, $H_{9α}$), 2.92 (1H, dd, J=14.6, 6.2 Hz, $H_{14α}$), 3.06 (1H, d, J=2,8 Hz, 7-OH), 3.29 (3H, s, OMe), 3.96 (1H, ddd, J=10.0, 4.0, 1.6 Hz, $H_7$), 4.16 (1H, d, J=11.6 Hz, $H_{1'}$), 4.33 (1H, d, J=11.6 Hz, $H_{1'}$), 4.38 (1H, d, J=3.6 Hz, $_2$), 4.53–4.58 (2H, m, $H_{13}$ and $H_{10}$), 4.98–5.01 (1H, m, $H_{20b}$), 5.11 (1H, ddd, J=17.2, 3.8, 1.4 Hz, $H_{20c}$), 5.92 (1H, ddt, J=17.2, 10.4, 6.8 Hz, $H_{4a}$), 6.80 (2H, d, J=8.8 Hz, $H_{4'}$), 7.22 (2H, d, J=8.8 Hz, $H_{3'}$).

Ketone 19 ($P_2$=PMB, $P_{13}$=TBS, $P_{10}$=TES, $P_7$=$CO_2$Et). To a stirred solution of ketone 19 ($P_2$=PMB, $P_{13}$=TBS, $P_{10}$=TES, $P_7$=H) (23 mg, 33 μmol) in $CH_2Cl_2$ (3 ml) and pyridine (240 μl, 3.0 mmol) at −40° C., was added a solution of phosgene (~50 μl at 5.5 M in $CH_2Cl_2$). The resulting mixture was allowed to stir at −10° C. for 1.5 hr, then EtOH (300 μl) was added. The reaction mixture was stirred at room temperature for 1 hr, then was treated with $Na(CO_3$ (2 ml). The mixture was extracted with EtOAc. The organic layer was washed with brine, was dried over $Na_2SO_4$ then was concentrated under reduce pressure. The crude product was subjected to flash chromatography (9:1 Hex-EtOAc) to afford 25 mg (99%) of ketone 19 ($P_2$=PMB, $P_{13}$=TBS, $P_{10}$=TES, $P_7$=$CO_2$Et) as a white solid. Mp. 121° C.; $^1$H ($C_6D_6$, 400 MHz, VR-2-73-2) δ 0.03 (3H, s, DMS), 0.12 (3H, s, DMS), 0.62 (6H, q, J=8.0 Hz, TES), 0.99 (9H, t, J=8.0 Hz, TES), 1.01 (9H, s, tBu), 1.01 (3H, t, J=7.2 Hz, $CO_2$Et-$CH_3$), 1.12 (3H, s, 17-Me), 1.19 (3H, s, 19-Me), 1.29 (3H, s, 16-Me), 1.50–1.56 (2H, m, $H_6$), 1.97 (1H, dd, J=11.4, 4.6 Hz, $H_{9β}$), 2.10 (1H, dd, J=8.4, 3.6 Hz, $H_1$), 2.13–2.19 (2H, m, $H_5$), 2.24 (3H, d, J=1.2 Hz, 18-Me), 2.27–2.35 (1H, ddd, J=14.8, 9.4, 9.4 Hz, $H_{14β}$), 2.95 (1H, t, J=11.4 Hz, $H_{9α}$), 2.96 (1H, dd, J=14.8, 6.4 Hz, $H_{14α}$), 3.29 (3H, s, OMe), 3.95 (2H, dq, J=18.0, 7.2 Hz, $Co_2$Et-$CH_2$), 4.29 (2H, s, $H_{1'}$), 4.39 (1H, d, J=3.6 Hz, $H_2$), 4.55 (1H, dd, J=11.4, 4.6 Hz, $H_{10}$), 4.58–4.63 (1H, m, $H_{13}$), 4.86–4.89 (1H, m, $H_{20b}$), 4.94 (1H, ddd, J=17.2, 3.4, 1.6 Hz, $H_{20c}$), 5.69 (1H, dddd, J=17.2, 10.4, 6.8, 6.8 Hz, $H_{4a}$), 5.76 (1H, t, J=6.2 Hz, $H_7$), 6.80 (2H, d, J=8.8 Hz, $H_{4'}$), 7.20 (2H, d, J=8.8 Hz, $H_{3'}$); $^{13}$C (CDCl$_3$, 100 MHz, VR-2-76) δ −5.0, −4.1, 5.0, 6.8, 14.2, 14.8, 16.2, 18.3, 26.1, 28.1, 28.2, 29.7, 30.6, 37.1, 47.5, 50.6, 54.7, 55.3, 63.9, 66.3, 68.3, 70.1, 74.9, 84.1, 113.9, 114.7, 128.8, 129.8, 130.3, 134.1, 137.9, 145.1, 155.3, 159.5, 212.3.

Ketone 19 ($P_2$=H, $P_{13}$=TBS, $P_{10}$=TES, $P_7$=$CO_2$Et). To a stirred suspension of ketone 19 ($P_2$=PMB, $P_{13}$=TBS, $P_{10}$=TES, $P_7$=$CO_2$Et) (13.7 mg, 18 μmol) in $CH_2Cl_2$ (1.8 ml) and water (180 μl) at 0° C., was added DDQ(12 mg, 53 μmol, 3 eq.). The resulting mixture was allowed to stir at −10° C. for 1.5 hr, then EtOH (300 μl) was added. The reaction mixture was stirred at room temperature for 5 hrs, then was treated with $Na_2S_2O_3$ solution (1 ml) and $NaHCO_3$ solution (1 ml). The mixture was extracted with EtOAc. The organic layer was washed with brine, dried over $Na_2SO_4$ then was concentrated under reduce pressure. The crude product was subjected to flash chromatography (95:5 Hex-EtOAc) to afford 10 mg (83%) of ketone 19 ($P_2$=H, $P_{13}$=TBS, $P_{10}$=TES, $P_7$=$CO_2$Et) as a colorless oil. $^1$H (CDCl$_3$, 500 MHz, VR-2-166-3) δ 0.07 (3H, s, DMS), 0.08 (3H, s, DMS), 0.56 (6H, q, J=8.0 Hz, TES-$CH_2$), 0.92 (9H, t, J=8.0 Hz, TES-$CH_3$), 0.96 (9H, s, tBu), 1.09 (3H, s, 17-Me), 1.14–1.20 (1H, m, $H_6$), 1.31 (3H, t, J=7.0 Hz, $CO_2$Et-$CH_3$), 1.40 (3H, s, 19-Me), 1.42–1.49 (1H, m, $H_6$), 1.55 (3H, s, 16-Me), 1.71 (1H, dd, J=12.5, 4.5 Hz, $H_{9β}$), 1.83 (3H, d, J=0.5 Hz, 18-Me), 1.89 (1H, dd, J=14.9, 6.0 Hz, $H_{14α}$), 2.03 (1H, dd, J=8.8, 4.3 Hz, $H_1$), 1.99–2.12 (2H, m, $H_5$), 2.21 (1H, ddd, J=14.9, 8.8, 8.7 Hz, $H_{14β}$), 2.50 (1H, dd, J=12.5, 11.5 Hz, $H_{9α}$), 2.80 (d, 1H, J=10.5 Hz, 2-OH), 4.20 (2H, dq, J=7.0, 2.0 Hz, $CO_2$Et-$CH_2$), 4.40 (1H, broad dd, J=8.8, 6.0 Hz, $H_{13}$), 4.47 (1H, dd, J=11.5, 4.5 Hz, $H_{10}$), 4.55 (1H, dd, J=10.5, 4.3 Hz, $H_2$), 4.92 (1H, dd, J=10.0, 1.8 Hz, $H_{20}$), 4.98 (1H, dd, J=17.0, 1.8 Hz, $H_{20}$), 5.28 (1H, d, J=8.5 Hz, $H_7$), 5.73 (1H, dddd, J=17.0, 10.0, 6.5, 6.5 Hz, $H_{4a}$); $^{13}$C (CDCl$_3$, 125 MHz, VR-2-166-3) δ −5.0, 4.2, 4.9, 6.8, 14.2, 15.2, 16.2, 18.2, 26.0, 27.7, 28.0, 28.3, 30.6, 37.0, 47.3, 54.6, 54.8, 64.0, 66.2, 67.8, 70.3, 83.6, 114.8, 135.2, 137.7, 144.3, 155.3, 217.3.

Ketone 20 ($P_2$=PMB). To a solution of 1.5 g (4.23 mmol)of 15 ($P_2$=PMB, $P_{10}$=H) in 10 ml of DMF at 0° C. was slowly added 2.07 g (5.55 mmol) of PDC (in three portions). The temperature was then allowed to rise at room temperature. After 2 h, the mixture was poured into 10 ml of water and extracted with 3×50 ml of ethyl acetate. The combined organic layers were dried over $Na_2SO_4$ and concentrated. Flash chromatography (hexane/ethyl acetate 7:3) gave 1.48 g (99%) of the ketone 20 ($P_2$=PMB) as a pale yellow solid. $^1$H NMR (500 MHz, CDCl$_3$), δ (ppm): 1.05 (s, 3H, 16Me), 1.16 (s, 3H, 17Me), 1.61 (dt, J=2.3, 1.7, 1.7 Hz, 3H, 18Me), 2.04 (ddq, J=17.5, 2.8, 2.3 Hz, 1H, $H_{14β}$), 2.06 (m, 1H, H1), 2.09 (dddd, J=13.6, 11.3, 9, 2 Hz, 1H, $H_{8β}$), 2.37 (ddd, J=13.6, 10.7, 1.7 Hz, 1H, $H_{8α}$), 2.42 (ddd, J=19.2, 9, 1.7 Hz, 1H, $H_{9β}$), 2.46 (ddq, J=17.5, 3.4, 1.7 Hz, 1H, $H_{14α}$), 2.67 (ddd, J=19.2, 11.3, 10.7 Hz, 1H, $H_{9α}$), 3.14 (d, J=2 Hz, 1H, 3-OH), 3.81 (s, 3H, OMe), 4.00 (d, J=6.2 Hz, 3H, $H_{2β}$), 4.42 (d, J=0.7 Hz, 1H, Hb), 4.65 (d, J=10.7 Hz, 1H, Ha), 5.40 (m, J=1.7 Hz, 1H, H13), 6.89 (d, J=8.5 Hz, 2H, H2'), 7.28 (d, J=8.5 Hz, 2H, H1'); $^{13}$C NMR (100 MHz, CDCl$_3$), δ (ppm): 21.7, 22.0, 25.1, 25.4, 37.2, 41.1, 41.2, 49.1, 55.2, 69.9, 72.5, 83.9, 88.4, 113.8, 121.6, 129.3, 130.2, 136.5, 159.3, 218.6.

Alkene 22 ($P_2$=PMB, $P_{10}$=TES). To a mixture of 170 mg (0.47 mmol) of the above ketone 2 ($P_2$=PMB) in 3.8 ml of ether at 0° C. was slowly added 955 μl (0.95 mmol) of a 1M solution of LAH in ether. After 2 h, 1 ml of water, 1 ml of a 1M aqueous solution of NaOH and 2 ml of water were added successively and the mixture was stirred for 3 h at room temperature then filtered on celite, dried over $Na_2SO_4$ and concentrated. Flash chromatography (hexane/ethyl acetate 7:3) afforded 155 mg (91%) of 10-β-hydroxy compound. $^1$H NMR (500 MHz, CDCl$_3$), δ (ppm): 1.25 (s, 3H, 17Me), 1.31 (s, 3H, 16Me), 1.81 (m, J=2.2, 1.5 Hz, 3H, 18Me), 1.85 (dd, J=5.9, 5.5 Hz, 1H, H1), 1.97 (m, 1H, H9β), 2.00 (m, J=10.3, 1.8 Hz, 1H, H8β), 2.00 (m, J=18 Hz, 1H, H14β), 2.13 (m, 1H, H8α), 2.26 (dd, J=9.4, 2.2 Hz, 1H, H9α), 2.36 (dq, J=8, 1.8 Hz, 1H, H14α), 3.00 (br, 1H, 3-OH), 3.81 (s, 3H, OMe), 3.90 (d, J=5.9 Hz, 1H, H2β), 4.33 (d, J=11.4 Hz, 1H, Hb), 4.57 (d, J=11.4 Hz, 1H, Ha), 4.84 (dd, J=9.4, 8.4 Hz, 1H, H10α), 5.44 (m, J=1.5 Hz, 1H, H13), 6.87 (d, J=8.8 Hz, 2H, H2'), 7.26 (d, J=8.8 Hz, 2H, H1').

To a mixture of 98 mg (0.27 mmol) of the above diol in 93 mg (1.36 mmol) of imidazole and 2.7 ml of DMF was added 92 µl (0.55 mmol) of TESCl, the resulting mixture was stirred at room temperature for 14 h. After addition of 3 ml of methanol, the mixture was concentrated, diluted with 10 ml of hexane and filtered. The organic layer was concentrated to give after flash chromatography (hexane:ethyl acetate 9:1) 126 mg (98%) of pure 10-β-protected alkene 22 ($P_2$=PMB, $P_{10}$=TES) as a colorless oil. $^1$H NMR(500 MHz, CDCl$_3$), δ (ppm): 0.59 (q, J=8 Hz, 6H, CH$_2$ 10-TES), 0.95 (t, J=8 Hz, 9H, CH$_3$ 10-TES), 1.20 (s, 3H, 17Me), 1.25 (s, 3H, 16Me), 1.77 (td, J=2.2, 2.2, 1.6 Hz, 3H, 18Me), 1.81 (dd, J=6.1, 5.8 Hz, 1H, H1), 1.90 (m, 1H, H9β), 1.97 (m, J=18.2 Hz, 1H, H14β), 2.00 (m, 1H, H8β), 2.08 (ddd, J=14.1, 7.4, 1 Hz, 1H, H8α), 2.15 (ddd, J=14.1, 9.3, 3.5 Hz, 1H, H9α), 2.32 (dd, J=18.2, 3.2 Hz, 1H, H14α), 2.94 (d, J=1.3 Hz, 1H, 3-OH), 3.78 (s, 3H, OMe), 3.86 (d, J=6.1 Hz, 1H, H2β), 4.31 (d, J=11.2 Hz, 1H, Hb), 4.55 (d, J=11.2 Hz, 1H, Ha), 4.79 (dd, J=9.3, 9 Hz, 1H, H10α), 5.37 (ddq, J=3.5, 3.2, 1.6 Hz, 1H, H13), 6.85 (d, J=8.6 Hz, 2H, H2'), 7.24 (d, J=8.6 Hz, 2H, H1'); $^{13}$C NMR (100 MHz, CDCl$_3$), δ (ppm): 5.2, 6.9, 22.8, 23.2, 25.6, 27.0, 34.0, 40.2, 40.3, 51.0, 55.2, 65.7, 67.9, 72.1, 85.8, 88.7, 113.7, 122.1, 129.1, 130.7, 139.9, 159.1.

Ketone 24 ($P_2$=PMB, $P_{10}$=TES, $P_{13}$=H). To a mixture of 70 mg (0.15 mmol) of the above alcohol 22 ($P_2$=PMB, $P_{10}$=TES) in 686 µl of dichloromethane was added 177 µl (0.6 mmol) of Ti(OiPr)$_4$, the resulting solution was stirred for 15 min at room temperature and 77 µl (0.752 mmol) of tBuOOH was introduced. After 1 h30 at room temperature, 500 µl (excess) of dimethylsulfide was added and the mixture was refluxed for 14 h. The solvents were removed under reduced pressure and the residue was dissolved in 5 ml of ethyl acetate and 300 µl of water. After stirring for 3 h at room temperature, the mixture was dried over Na$_2$SO$_4$, filtered through a cake of celite and concentrated. A plug chromatography (hexane/ethyl acetate 7:3) led to 77.8 mg (100%) of ketone 24 ($P_2$=PMB, $P_{10}$=TES, $P_{13}$=H) as a colorless oil. $^1$H NMR (400 MHz, CDCl$_3$), δ (ppm): 0.58 (q, J=8.1 Hz, 6H, CH$_2$ 10-TES), 0.95 (t, J=8.1 Hz, 3H, CH$_3$ 10-TES), 0.99 (s, 3H, 17Me), 1.59 (s, 3H, 16Me), 1.67 (d, J=1.8 Hz, 3H, 18Me), 1.85 (ddd, J=13.9, 6, 3.3 Hz, 1H, H9α), 1.94 (m, J=6.6, 2.6 Hz, 1H, H8α), 2.04 (dd, J=7.3, 3.3 Hz, 1H, H1), 2.20 (ddd, J=14.3, 7.7, 3.3 Hz, 1H, H8β), 2.21 (dd, J=15.8, 3.3 Hz, 1H, H14α), 2.29 (m, 1H, H9β), 2.62 (ddd, J=15.8, 10.5, 7.3 Hz, 1H, H14β), 3.80 (s, 3H, OMe), 4.07 (dd, J=10.5, 1.8 Hz, 1H, H13β), 4.25 (d, J=11.4 Hz, 1H, Hb), 4.37 (d, J=3.3 Hz, 1H, H2β), 4.37 (d, J=11.4 Hz, 1H, Ha), 4.75 (dd, J=10.3, 6 Hz, 1H, H10α), 6.86 (d, J=8.8 Hz, 2H, H2'), 7.22 (d, J=8.8 Hz, 2H, H1').

Ketone 24 ($P_2$=PMB, $P_{10}$=TES, $P_{13}$=TBS). To a solution of 143 mg (0.3 mmol) of crude ketone 24 ($P_2$=PMB, $P_{10}$=TES, $P_{13}$=H) in 2 ml of pyridine at −25° C. was slowly added 134 µl (0.6 mmol) of TBSOTf. The mixture was then stirred at −10° C. for 3 h, dilute by 20 ml of hexane, quenched by addition of 1 ml of methanol and concentrated. The residue was dissolved in 20 ml of hexane and washed by 3 ml of a saturated aqueous solution of NaHCO$_3$. The aqueous layer was extracted by 10 ml of dichloromethane and 10 ml of ethyl acetate. The combined organic layers were dried over Na$_2$SO$_4$ and concentrated. Flash chromatography (hexane/ethyl acetate 9:1) afforded 178.3 mg (100%) of ketone 24 ($P_2$=PMB, $P_{10}$=TES, $P_{13}$=TBS). $^1$H NMR (400 MHz, CDCl$_3$), δ (ppm): 0.05 (s, 3H, CH$_3$ 13-TBS), 0.09 (s, 3H, CH$_3$ 13-TBS), 0.57 (q, J=7.8 Hz, 6H, CH$_2$ 10-TES), 0.95 (t, J=7.8 Hz, 9H, CH$_3$ 10-TES), 0.96 (s, 9H, (CH$_3$)$_3$ 13-TBS), 1.04 (s, 3H, 17Me), 1.59 (s, 3H, 16Me), 1.60 (d, J=1.1 Hz, 3H, 18Me), 1.83 (ddd, J=13.7, 6.6, 3.4 Hz, 1H, H9α), 1.94 (m, J=15.8 Hz, 1H, H14β), 1.98 (dd, J=7.4, 3 Hz, 1H, H1), 2.16 (dd, J=14, 3.4 Hz, 1H, H8β), 2.22 (m, 1H, H8α), 2.25 (dd, J=15.8, 3.8 Hz, 1H, H14α), 2.27 (m, J=7 Hz, 1H, H9β), 3.80 (s, 3H, OMe),4.17 (d, J=11.5 Hz, 1H, Hb), 4.33 (d, J=3 Hz, 1H, H2β), 4.38 (d, J=11.5 Hz, 1H, Ha), 4.42 (m, J=9.1, 1.1 Hz, 1H, H13β), 4.77 (dd, J=10.8, 6.6 Hz, 1H, H10α), 6.84 (d, J=8.6 Hz, 2H, H2'), 7.23 (d, J=8.6 Hz, 2H, H1').

Ketone 26 ($P_2$=PMB, $P_9$=H). To a cooled solution of ketone 20 (866 mg, 2.4 mmol) in 24 ml of THF and 1.7 ml (9.73 mmol) of HMPA at −10° C. was added 9.73 ml (9.73 mmol) of a 1M solution of L; HMDS in THF The mixture was stirred for 1 h then cooled to −78° C. and 1 ml (6.08 mmol) of a solution of TESCl was added. The resulting mixture was stirred for 1 h at −78° C. and poured into 100 ml of hexane. The organic layer was then washed by 20 ml of a saturated aqueous solution of NaHCO$_3$ followed by 20 ml of brine. The combined aqueous layers were extracted by 50 ml of hexane. The organic layer was dried over Na$_2$SO$_4$ and concentrated to give 1.87 g of crude compound as a yellow oil (3,10 bis TES enol-ether). $^1$H NMR (500 MHz, CDCl$_3$), δ (ppm): 0.46 (q, J=7.6 Hz, 6H, CH$_2$ TES), 0.72 (q, J=7.6 Hz, 6H, CH$_2$ TES), 0.83 (t, J=7.6 Hz, 9H, CH$_3$ TES), 0.94 (s, 3H, 16Me), 1.00 (t, J=7.6 Hz, 9H, CH$_3$ TES), 1.17 (s, 3H, 17Me), 1.67 (m, J=1.6, 1.8 Hz, 3H, 18Me), 1.96 (m, 2H, H14β-H1), 2.28 (m, J=16.7, 1.8 Hz, 1H, H14α), 2.30 (dd, J=16, 2.1 Hz, 1H, H8), 2.41 (dd, J=16, 2.5 Hz, 1H, H8), 3.81 (s, 3H, OMe), 3.82 (dd, J=5.2, 0.9 Hz, 1H, H2β), 4.26 (d, J=10.8 Hz, 1H, Hb), 4.38 (d, J=10.8 Hz, 1H, Ha), 4.45 (dd, J=2.5, 2.1 Hz, 1H, H9), 5.17 (m, 1H, H13), 6.86 (d, J=8.7 Hz, 2H, H2'), 7.27 (d, J=8.7 Hz, 2H, H1').

To a mixture of crude (1.87 g) and 613 mg (7.3 mmol) of NaHCO$_3$ in 50 ml of hexane was added at 0° C. 900 mg (3.6 mmol) of mCPBA. The mixture was stirred at 0° C. for 4 h and diluted by 100 ml of hexane. The organic layer was washed twice with 50 ml of a saturated solution of NaHCO$_3$/Na$_2$S$_2$O$_3$ (1:1), dried over Na$_2$SO$_4$ and concentrated.

To a solution of the above crude in 10 ml of THF at 0° C. was added 12 ml (12 mmol) of a 1M solution of TBAF in THF The resulting solution was stirred for 1 h at room temperature. The mixture was diluted with 100 ml of ethyl acetate, washed with 20 ml of a saturated aqueous solution of NaHCO$_3$, 20 ml of brine, dried over Na$_2$SO$_4$ and concentrated. A flash chromatography (hexanelethyl acetate 1:1) led to 690 mg (76% over 3 steps) of ketone 26 ($P_2$=PMB, $P_9$=H). $^1$H NMR (300 MHz, CDCl$_3$), δ (ppm): 0.99 (s, 3H, 16Me), 1.16 (s, 3H, 17Me), 1.69 (m, J=1.8 Hz, 3H, 18Me), 2.07 (m, J=2.3 Hz, 1H, H14β), 2.09 (m, 1H, H1), 2.33 (dd, J=15.8, 1.8 Hz, 1H, H8α), 2.44 (ddd, J=15.8, 7, 1.8 Hz, 1H, H8β), 2.48 (m, 1H, H14α), 2.91 (br, 1H, 9-OH), 2.35 (br, 1H, 3-OH), 3.81 (s, 3H, OMe), 4.01 (d, J=5.9 Hz, 1H, H2β), 4.02 (m, 1H, H9β), 4.42 (d, J=11.2 Hz, 1H, Hb), 4.64 (d, J=11.2 Hz, 1H, Ha), 5.45 (m, 1H, H13), 6.90 (d, J=8.3 Hz, 2H, H2'), 7.29 (d, J=8.3 Hz, 2H, H1').

Ketone 26 ($P_2$=PMB, $P_9$=TES). To a solution of 718 mg (1.26 mmol) of crude above ketone 26 ($P_2$=PMB, $P_9$=H) in 13.5 ml of dichloromethane and 2 ml (14.13 mmol) of triethylamine at 0° C. was slowly added a catalytic amount of DMAP and 710 µl (4.2 mmol) of TESCl. The mixture was stirred under nitrogen for 1 h. After addition of 3 ml of methanol, the resulting mixture was stirred for 15 min at room temperature and concentrated. The crude was dissolved in 100 ml of hexane and the salts were filtered. The organic layer was then dried over Na$_2$SO$_4$ and concentrated to give after flash chromatography (hexane/ethyl acetate 8:2) 604 mg (88% over 2 steps) of ketone 26 ($P_2$=PMB, $P_9$=TES) as a colorless oil. $^1$H NMR (500 MHz, CDCl$_3$), δ (ppm): 0.60 (q, J=8 Hz, 6H, CH$_2$ 9-TES), 0.95 (s, 3H, 16Me), 0.98 (t, J=8 Hz, 9H, CH$_3$ 9-TES), 1.30 (s, 3H, 17Me), 1.67 (td, J=2.2, 2.2, 1.3 Hz, 3H, 18Me), 2.20 (m, J=6.1 Hz, 1H, H1), 2.22 (ddq, J=14.2, 3.2, 2.2 Hz, 1H, H14β), 2.31 (dd, J=15.3, 2.2 Hz, 1H, H8α), 2.42 (ddd, J=15.3, 7.7, 1.3 Hz, 1H, H8β), 2.47 (ddq, J=14.2, 3.5, 2.2 Hz, 1H, H14α), 3.10 (br, 1H, 3-OH), 3.80 (s, 3H, OMe), 3.95 (d, J=6.1 Hz, 1H, H2β), 4.05 (dd, J=7.7, 2.2 Hz, 1H, H9β), 4.37 (d, J=11.2 Hz, 1H, Hb), 4.67 (d, J=11.2 Hz, 1H, Ha), 5.40 (ddq, J=3.5, 3.2, 1.3 Hz, 1H, H13), 6.86 (d, J=8.6 Hz, 2H, H2'), 7.28 (d, J=8.6 Hz, 2H, H1').

Triol 27 ($P_2$=PMB, $P_9$=$P_{10}$=H). To a mixture of 590 mg (1.58 mmol) of 3,9-dihydroxyketone 26 in 20 ml of ether at 0° C. was slowly added 2.4 ml (2.4 mmol) of a 1M solution of lithiumaluminiumhydride in ether. After 2 h, the reaction was quenched by addition of 3 ml of water, 3 ml of a 1M solution of NaOH and 6 ml of water. The resulting solution was stirred for 2 h at room temperature and diluted with 100 ml of ethyl acetate. After filtration through a cake of celite the organic layer was dried over $Na_2SO_4$ and concentrated to give 530 mg (90%) of triol 27 as a colorless oil.

Alkene 27 ($P_2$=PMB, $P_9$=TES, $P_{10}$=H). To a solution of 530 mg (1.41 mmol) of the above triol 27 ($P_2$=PMB, $P_9$=$P_{10}$=H) in 26 ml of dichloromethane and 2 ml (14.13 mmol) of triethylamine at 0° C. was slowly added a catalytic amount of DMAP and 355 µl (2.11 mmol) of TESCl. The mixture was stirred under nitrogen for 1 h. After addition of 5 ml of methanol, the resulting mixture was stirred for 15 min at room temperature then concentrated. The crude was dissolved in 150 ml of hexane and filtered. The organic layer was concentrated to give after flash chromatography (exane/ethyl acetate 8:2) 649 mg (94%) of diol 27 ($P_2$=PMB, $P_9$=TES, $P_{10}$=H) as white solid. m.p. 90–92° C.; $^1$H NMR (400 MHz, $CDCl_3$), δ (ppm): 0.59 (q, J=8.1 Hz, 6H, $CH_2$ 9-TES), 0.96 (t, J=8.1 Hz, 9H, $CH_3$ 9-TES), 1.615 (s, 3H, 16Me), 1.21 (s, 3H, 17Me), 1.59 (br s, 1H, 10-OH), 1.78 (t, J=5.7 Hz, 1H, H1), 1.81 (dt, J=2.4, 1.9, 1.9 Hz, 3H, 18Me), 1.97 (ddq, J=18.2, 3.4, 2.4 Hz, 1H, H14β), 1.99 (dd, J=14.8, 6.3 Hz, 1H, H8α), 2.28 (dd, J=14.8, 9.1 Hz, 1H, H8β), 2.32 (ddq, J=18.2, 3.4, 1.9 Hz, 1H, H14α), 3.00 (br s, 1H, 3-OH), 3.79 (s, 3H, OMe), 3.81 (d, J=5.7 Hz, 1H, H2β), 4.29 (d, J=11 Hz, 1H, Hb), 4.40 (ddd, J=9.1, 7.7, 6.3 Hz, 1H, H9β), 4.45 (t, J=7.7 Hz, 1H, H10α), 4.54 (d, J=11 Hz, 1H, Ha), 5.40 (m, J=3.4 Hz, 1H, H13), 6.85 (d, J=8.6 Hz, 2H, H2'), 7.26 (d, J=8.6 Hz, 2H, H1').

Ketone 28 ($P_2$=PMB, $P_9$=TES, $P_{10}$=H, $P_{13}$=H). To a solution of 400 mg (0.83 mmol) of the above diol 27 ($P_2$=PMB, $P_9$=TES, $P_{10}$=H) in 5 ml of dichloromethane at 0° C. was added 987 µl (3.31 mmol) of Ti(OiPr)$_4$, after 30 min, 425 µl (4.15 mmol) of tBuOOH was added. The resulting mixture was stirred for 4 h at 0° C. and 1.24 ml (16.6 mmol) of dimethyl)sulfide was introduced and the resulting mixture was stirred at room temperature for 14 h. The mixture was concentrated and the crude residue was dissolved in 200 ml of THF. 3 ml of water was added and after 3 h, the mixture was dried over $Na_2SO_4$, filtered and concentrated to give 496.4 mg of crude compound 28 ($P_2$=PMB, $P_9$=TES, $P_{10}$=H, $P_{13}$=H) as a colorless oil.

Ketone 28 ($P_2$=PMB, $P_9$=TES, $P_{10}$=H, $P_{13}$=TBS). To a solution of 496.4 mg of crude ketone 28 ($P_2$=PMB, $P_9$=TES, $P_{10}$=H, $P_{13}$=H) in 3.3 ml of pyridine at −45° C. was added 420 µl (1.82 mmol) of TBSOTf. The reaction was stirred at −10° C. for 2 h, diluted with 20 ml of hexane, quenched by addition of 500 µl of methanol and stirred for 30 min. The volatils were concentrated and the residue was dissolved in 20 ml of hexane and filtered. The organic layer was concentrated to lead after flash chromatography (hexane/ethyl acetate 9:1) to 450 mg (89% over 2 steps) of pure ketone 28 ($P_2$=PMB, $P_9$=TES, $P_{10}$=H, $P_{13}$=TBS) as a pale yellow solid. m.p. 64–66° C.; $^1$H NMR (500 MHz, $CDCl_3$), δ (ppm): 0.06 (s, 3H, $CH_3$ 13-TBS), 0.10 (s, 3H, $CH_3$ 13-TBS), 0.58 (q, J=7.9 Hz, 6H, $CH_2$ 9-TES), 0.95 (t, J=7.9 Hz, 9H, $CH_3$ 9-TES), 0.96 (s, 9H, $(CH_3)_3$ 13-TBS), 1.10 (s, 3H, 17Me), 1.52 (s, 3H, 16Me), 1.70 (d, J=1.1 Hz, 3H, 18Me), 1.98 (dd, J=7.3, 2.9 Hz, 1H, H1), 2.04 (dd, J=16.9, 4.4 Hz, 1H, H8β), 2.07 (d, J=2.3 Hz, 1H, 10-OH), 2.26 (dd, J=14.9, 5.7 Hz, 1H, H14α), 2.30 (dd, J=14.9, 7.3 Hz, 1H, H14β), 2.35 (dd, J=16.9, 12 Hz, 1H, H8α), 3.80 (s, 3H, OMe), 4.16 (d, J=2.9 Hz, 1H, H2β), 4.24 (d, J=12 Hz, 1H, Hb), 4.39 (ddd, J=12, 8.8, 4.4 Hz, 1H, H9β), 4.44 (d, J=12 Hz, 1H, Ha), 4.46 (m, 1H, H13β), 4.55 (dd, J=8.8, 2.3 Hz, 1H, H10α), 6.86 (d, J=8.6 Hz, 2H, H2'), 7.22 (d, J=8.6 Hz, 2H, H1'); $^{13}$C NMR(100 MHz, $CDCl_3$), δ (ppm): −5.1, −4.2, 4.9, 6.7, 15.9, 18.1, 21.4, 22.3, 25.4, 25.7, 41.1, 48.4, 48.9, 55.2, 69.9, 72.4, 76.5, 84.6, 86.9, 113.7, 121.1, 128.3, 130.2, 136.8, 159.2, 216.2.

Ketone 28 ($P_2$=PMB, $P_9$=TMS, $P_{10}$=TES, $P_{13}$=TBS). To a solution of 218 mg (0.35 mmol) of ketone28 ($P_2$=PMB, $P_9$=TES, $P_{10}$=H, $P_{13}$=TBS) in 6.4 ml THF at −78° C. was added 92 µl (0.53 mmol) HMPA and 530 µl (0.53 mmol) of a 1M solution of LiHMDS in THF. The mixture was stirred at −20° C. for 1 h and cooled to −78° C. 148 µl (1.06 mmol) of triethylamine and 90 µl (0.7 mmol) of TMSCl were successively added. After 30 min, the mixture was diluted with 20 ml of hexane, washed by 10 ml of a 1:1 aqueous solution of $NaHCO_3$ and brine. The aqueous layer was extracted by 20 ml of a solution of hexane/ethyl acetate (8:2), the combined organic layers were dried over $Na_2SO_4$ and concentrated. After flash chromatography (hexane/ethyl acetate 9:1), 207 mg (93%) of ketone 28 ($P_2$=PMB, $P_9$=TMS, $P_{10}$=TES, $P_{13}$=TBS) was obtained as a colorless oil. $^1$H NMR (400 MHz, $C_6D_6$), δ (ppm): 0.04 (s, 3H, $CH_3$ 13-TBS), 0.13 (s, 9H, $CH_3$ 9-TMS), 0.14 (s, 3H, $CH_3$ 13-TBS), 0.68 (q, J=8.1 Hz, 6H, $CH_2$ 10-TES), 1.04 (t, J=8.1 Hz, 9H, $CH_3$ 10-TES), 1.08 (s, 9H, $(CH_3)_3$ 13-TBS), 1.10 (s, 3H, 17Me), 1.64 (s, 3H, 16Me), 1.89 (s, 3H, 18Me), 2.08 (dd, J=8.1, 2.9 Hz, 1H, H1), 2.15 (dd, J=16.9, 4.4 Hz, 1H, H8β), 2.40 (ddd, J=14.7, 10.3, 8.1 Hz, 1H, H14β), 2.63 (dd, J=16.9, 11.7 Hz, 1H, H8α), 2.75 (dd, J=14.7, 5.5 Hz, 1H, H14α), 3.29 (s, 3H, OMe), 4.18 (d, J=11.7 Hz, 1H, Hb), 4.30 (d, J=2.9 Hz, 1H, H2β), 4.48 (ddd, J=11.7, 8.4, 4.4 Hz, 1H, H9β), 4.49 (d, J=11.7 Hz, 1H, Ha), 4.55 (dd, J=10.3, 5.5 Hz, 1H, H13β), 4.75 (d, J=8.4 Hz, 1H, H10α), 6.76 (d, J=8.4 Hz, 2H, H2'), 7.18 (d, J=8.6 Hz, 2H, H1').

Ketone 29 ($P_2$=PMB, $P_9$=TMS, $P_{10}$=TES, $P_{13}$=TBS). To a solution of 103 mg (0.15 mmol) of ketone 28 ($P_2$=PMB, $P_9$=TMS, $P_{10}$=TES, $P_{13}$=TBS) in 5 ml of THF and 94 µl (1.5 mmol) of methyliodide at −78° C. was slowly added 3 ml (1.5 mmol) of a 0.5M solution of KHMDS in THF. The reaction mixture was stirred for 4 h at −78° C. and diluted by addition of 50 ml of hexane and extracted by 10 ml of a saturated aqueous solution of $NaHCO_3$. The organic layer was dried over $Na_2SO_4$ and concentrated to afford 105.4 mg(100%) of $β_{19}$-methyl ketone 29 ($P_2$=PMB, $P_9$=TMS, $P_{10}$=TES, $P_{13}$=TBS) as a colorless oil. $^1$H NMR (500 MHz, $C_6D_6$), δ (ppm): 0.04 (s, 3H, $CH_3$ 13-TBS), 0.14 (s, 3H, $CH_3$ 13-TBS), 0.22 (s, 9H, $CH_3$ 9-TMS), 0.75 (q, J=8.1 Hz, 6H, $CH_2$ 10-TES), 1.04 (t, J=8.1 Hz, 9H, $CH_3$ 10-TES), 1.07 (d, J=7.4 Hz, 3H, 19Me), 1.09 (s, 9H, $(CH_3)_3$ 13-TBS), 1.11 (s, 3H, 17Me), 1.65 (s, 3H, 16Me 1.88 (s, 3H, 18Me), 2.12 (dd, J=8.1, 3.1 Hz, 1H, H1), 2.36 (ddd, J=14.2, 10.1, 8.1 Hz, 1H, H14β), 2.45 (dd, J=10.9, 7.4 Hz, 1H, H8α), 2.79 (dd, J=14.2, 5.5 Hz, 1H, H14α), 3.28 (s, 3H, OMe), 4.07 (d, J=11.1 Hz, 1H, Hb), 4.24 (dd, J=10.9, 8.1 Hz, 1H, H9β), 4.28 (d, J=3.1 Hz, 1H, H2β), 4.45 (d, J=11.1 Hz, 1H, Ha), 4.54 (dd, J=10.1, 5 Hz, 1H, H13β), 4.73 (d, J=8.1 Hz, 1H, H10α), 6.80 (d, J=8.6 Hz, 2H, H2'), 7.29 (d, J=8.6 Hz, 2H, H1'); $^{13}$C NMR (100 MHz, $CDCl_3$) δ (ppm): −5.1, −4.1, 4.8, 6.8, 14.9, 18.1, 19.0, 25.9, 26.6, 28.1, 29.4, 29.7, 37.1, 41.2, 45.5, 53.0, 55.2, 67.1, 69.8, 70.6, 95.5, 113.7, 129.3, 130.4, 137.1, 137.5, 159.1, 210.2.

Ketone 29 ($P_2$=H, $P_9$=TMS, $P_{10}$=TES, $P_{13}$=TBS). To a mixture of 1.07 g (1.5 mmol) of ketone 29 ($P_2$=PMB, $P_9$=TMS, $P_{10}$=TES, $P_{13}$=TBS) in 137.5 ml of dichloromethane/water (9:1) at 0° C. was added 1.03 g (4.5 mmol) of DDQ. The resulting mixture was stirred at 0° C.

for 4 h then diluted by 20 ml of ethyl acetate and washed by 3×50 ml of a 1:1 solution of NaHCO$_3$/Na$_2$S$_2$O$_3$. The combined aqueous layers were extracted by 100 ml of ethyl acetate. The organic layer was dried over Na$_2$SO$_4$ and concentrated to afford 1.04 g of the crude ketone 29 (P$_2$=H, P$_9$=TMS, P$_{10}$=TES, P$_{13}$=TBS) as a colorless oil. $^1$H NMR (400 MHz, C$_6$D$_6$), δ (ppm): 0.008 (s, 3H, CH$_3$ 13-TBS), 0.09 (s, 3H, CH$_3$ 13-TBS), 0.18 (s, 9H, CH$_3$ 9-TMS), 0.68 (q, J=7.9 Hz, 6H, CH$_2$ 10-TES), 1.01 (t, J=7.9 Hz, 9H, CH$_3$ 10-TES), 1.04 (s, 3H, 17Me), 1.05 (d, J=7.3 Hz, 3H, 19Me), 1.06 (s, 9H, (CH$_3$)$_3$ 13-TBS), 1.57 (s, 3H, 16Me), 1.79 (s, 3H, 18Me), 2.00 (dd, J=7.5, 3.7 Hz, 1H, H1), 2.13 (dd, J=15.3, 4.9 Hz, 1H, H14α), 2.26 (ddd, J=15.3, 10.4, 7.5 Hz, 1H, H14β), 2.47 (dq, J=11, 7.3 Hz, 1H, H8α), 3.45 (d, J=7.9 Hz, 1H, 2-OH), 4.22 (dd, J=11, 8.6 Hz, 1H, H9β), 4.40 (dd, J=10.4, 4.9 Hz, 1H, H13β), 4.46 (dd, J=7.9, 3.7 Hz, 1H, H2β), 4.66 (d, J=8.6 Hz, 1H, H10α).

Ketone 29 (P$_2$=P$_9$=TMS, P$_{10}$=TES, P$_{13}$=TBS). To a solution of 1.04 g of crude 29 (P$_2$=H, P$_9$=TMS, P$_{10}$=TES, P$_{13}$=TBS) in 10 ml of pyridine was added a catalytic amount of DMAP and at −10° C. 420 μl (3.3 mmol) of TMSCl. After 1 h of reaction at 0° C., the mixture was diluted by 100 ml of hexane and washed twice with 20 ml of a saturated aqueous solution of NaHCO$_3$. The organic layer was then dried over Na$_2$SO$_4$ and concentrated. After flash chromatography (hexane/ethyl acetate 99.5:0.5), 856 mg (86% over 2 steps) of ketone 29 (P$_2$=P$_9$=TMS, P$_{10}$=TES, P$_{13}$=TBS) was obtained as a yellow oil. $^1$H NMR (500 MHz, C$_6$D$_6$), δ (ppm): 0.03 (s, 3H, CH$_3$ 13-TBS), 0.13 (s, 3H, CH$_3$ 13-TBS), 0.15 (s, 9H, CH$_3$ 2-TMS), 0.24 (s, 9H, CH$_3$ 9-TMS), 0.72 (dq, J=7.9, 2.7 Hz, 6H, CH$_2$ 10-TES), 1.04 (t, J=7.9 Hz, 9H, CH$_3$ 10-TES), 1.05 (s, 9H, (CH$_3$)$_3$ 13-TBS), 1.12 (s, 3H, 17Me), 1.19 (d, J=7.3 Hz, 3H, 19Me), 1.72 (s, 3H, 16Me), 1.86 (d, J=1.2 Hz, 3H, 18Me), 1.89 (dd, J=8.2, 3.4 Hz, 1H, H1), 2.30 (ddd, J=14.6, 10.3, 8.2 Hz, 1H, H14β), 2.44 (dq, J=10.7, 7.3 Hz, 1H, H8α), 2.68 (dd, J=14.6, 5.5 Hz, 1H, H14α), 4.35. (dd, J=10.7, 8.9 Hz, 1H, H9β), 4.54 (ddd, J=10.4, 5.5, 1.2 Hz, 1H, H13β), 4.66 (d, J=3.4 Hz, 1H, H2β), 4.72 (d, J=8.9 Hz, 1H, H10α).

In view of the above, it will be seen that the several objects of the invention are achieved.

As various changes could be made in the above compositions without departing from the scope of the invention, it is intended that all matter contained in the above description be interpreted as illustrative and not in a limiting sense.

What is claimed is:

1. A process for the preparation of a compound having the formula:

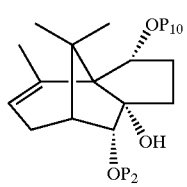

the process comprising treating a compound having the formula:

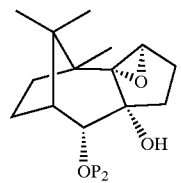

with a Lewis acid in the presence of a tertiary amine base, wherein P$_2$ is hydrogen or a hydroxy protecting group.

2. The process of claim 1 wherein the Lewis acid is TMSOTf.

3. The process of claim 1 wherein the tertiary amine base is triethyl amine.

4. The process of claim 1 wherein the Lewis acid is TMSOTf and the tertiary amine base is triethylamine.

5. A compound selected from the group consisting of:

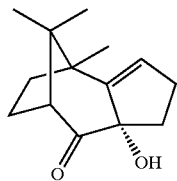

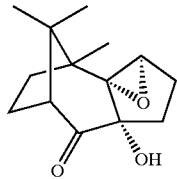

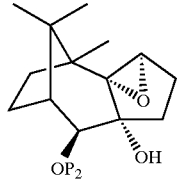

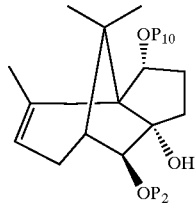

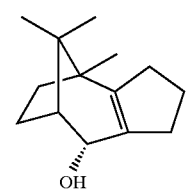

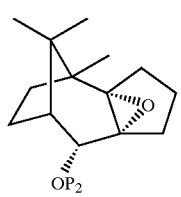
12
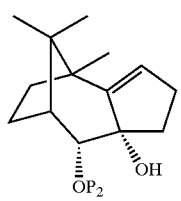
13
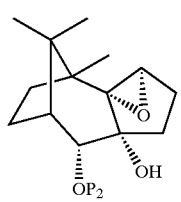
14
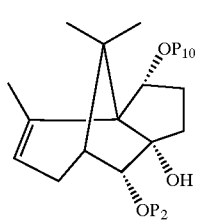
15
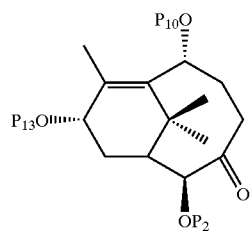
16
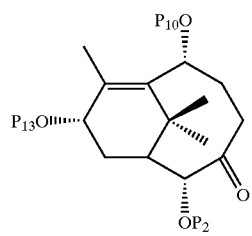
17
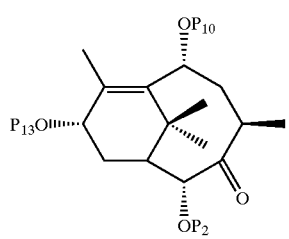
18
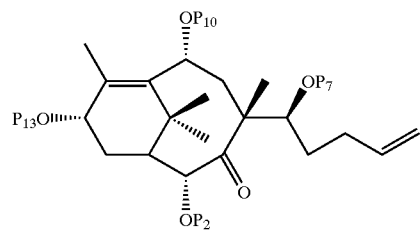
19
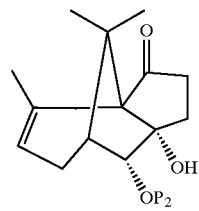
20
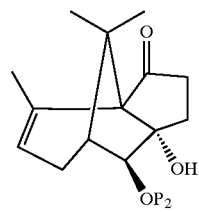
21
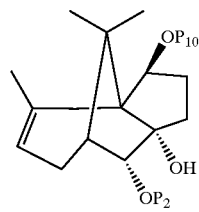
22
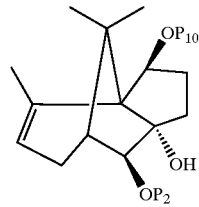
23
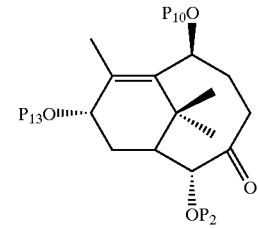
24
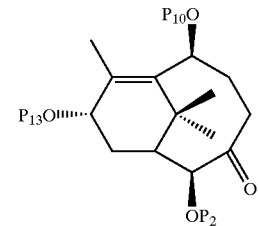
25

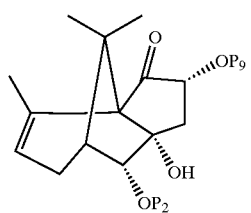
26
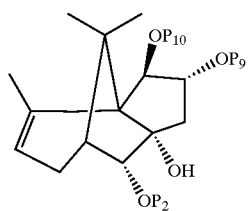
27
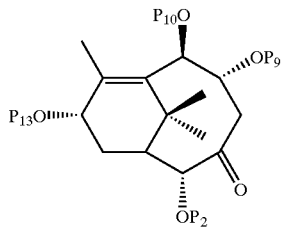
28
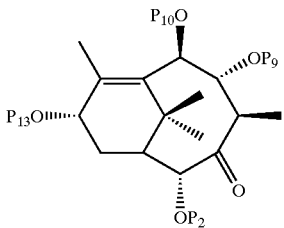
29
wherein $P_2$, $P_7$, $P_9$, $P_{10}$ and $P_{13}$ are independently selected from hydrogen and hydroxy protecting group.
* * * * *